United States Patent [19]
Guerry et al.

[11] Patent Number: 5,866,583
[45] Date of Patent: Feb. 2, 1999

[54] SUBSTITUTED 2,4-DIAMINOPYRIMIDINES

[75] Inventors: Philippe Guerry, Binningen; Henri Stalder, Basel; Pierre-Charles Wyss, Muttenz, all of Switzerland

[73] Assignee: Hoffmann-La Roche Inc., Nutley, N.J.

[21] Appl. No.: 842,459

[22] Filed: Apr. 24, 1997

[30] Foreign Application Priority Data

May 15, 1996 [EP] European Pat. Off. .............. 96107739

[51] Int. Cl.⁶ ........................ C07D 401/10; A61K 31/505
[52] U.S. Cl. .................... 514/275; 544/295; 544/238; 544/122; 544/123; 544/324; 544/296; 540/601; 540/481; 514/212; 514/183; 514/235.8; 514/236.5; 514/252; 514/269
[58] Field of Search .................... 544/324, 295, 544/122; 514/275, 212, 236.5; 540/601, 481

[56] References Cited

U.S. PATENT DOCUMENTS

| 3,341,541 | 9/1967 | Hoffer ................................. 260/256.4 |
| 4,013,644 | 3/1977 | Lenz ........................................ 260/240 |
| 4,515,948 | 5/1985 | Kompis et al. .......................... 544/325 |
| 4,594,199 | 6/1986 | Thottathil .............................. 260/502.4 |

FOREIGN PATENT DOCUMENTS

| 1188690 | 6/1985 | Canada . |
| 0 041 215 | 12/1981 | European Pat. Off. . |
| WO 92/08461 | 5/1992 | WIPO . |
| WO 96/16046 | 5/1996 | WIPO . |
| WO 96/40640 | 12/1996 | WIPO . |

OTHER PUBLICATIONS

Roth et al., J. Med. Chem. 32, 1989 pp. 1949–1958.
Nagakura et al., Phytochemistry, 32(3), 1993 pp. 761–765.
Tietze et al. Chemische Berichte, 125, 1992, pp. 2571–2576.
Yamaguchi et al., J. Am. Chem. Soc. 110, 1988, pp. 2186–2187.
D.P. Baccanari, Biochemistry 20, pp. 1710–1716 (1981).
P.G. Hartman et al. FEBA Letters 242, pp. 157–160 (1988).

Primary Examiner—John M. Ford
Attorney, Agent, or Firm—George W. Johnston; William H. Epstein; John P. Parise

[57] ABSTRACT

Compounds of formula I

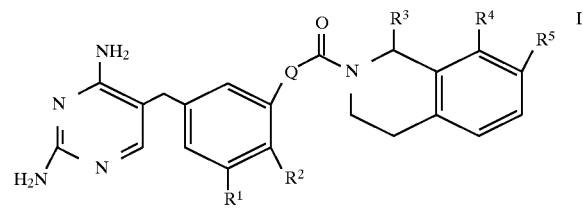

wherein $R^1$ is lower-alkoxy, $R^2$ is bromine, lower-alkoxy or hydroxy, $R^3$ is hydrogen, lower-alkyl, cycloalkyl, aryl, heterocyclyl, aralkyl, heterocyclyl-lower-alkyl or cyano, $R^4$ and $R^5$ each independently are hydrogen, lower-alkyl, lower-alkoxy, halogen, hydroxy, amino, di(lower alkyl) amino, cyano or nitro and Q is ethynylene or vinylene, or pharmaceutically usable salts thereof, the use of these compounds and their salts as therapeutically active substances; medicaments based on these substances and their production; the use of these substances as medicaments and for the production of antibacterially-active medicaments; as well as the manufacture of the compounds of formula I and their pharmaceutically acceptable salts and intermediates for their manufacture.

92 Claims, No Drawings

SUBSTITUTED 2,4-DIAMINOPYRIMIDINES

BACKGROUND OF THE INVENTION

FIELD OF THE INVENTION

The invention relates to substituted 2,4-diaminopyrimidines useful in treating infectious diseases.

SUMMARY OF THE INVENTION

The present invention relates to substituted 2,4-diaminopyrimidines of the formula

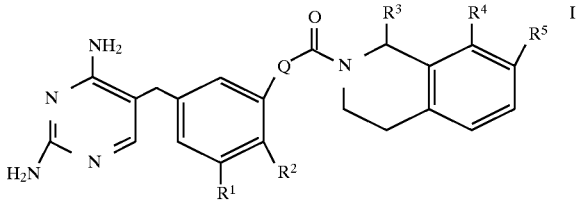

wherein $R^1$ is lower-alkoxy, $R^2$ is bromine, lower-alkoxy or hydroxy, $R^3$ is hydrogen, lower-alkyl, cycloalkyl, aryl, heterocyclyl, aralkyl, heterocyclyl-lower-alkyl or cyano, $R^4$ and $R^5$ each independently are hydrogen, lower-alkyl, lower-alkoxy, halogen, hydroxy, amino, di(lower alkyl) amino, cyano or nitro and Q is ethynylene or vinylene, as well as pharmaceutically usable salts thereof.

These compounds are novel and possess valuable antibiotic properties. They can be used for the control or prevention of infectious diseases. In particular, they exhibit a pronounced antibacterial activity, even against multiresistant, Gram-positive strains and against opportunistic pathogens such as, for example, *Pneumocystis carinii*. These compounds can also be administered in combination with known antibacterially-active substances and then exhibit synergistic effects. Typical combination partners are, for example, sulphonamides, with which the compounds of formula I or their salts can be admixed in various ratios.

Objects of the present invention are compounds of formula I and their pharmaceutically acceptable salts per se for use as therapeutically active substances; medicaments based on these substances, optionally in combination with sulphonamides, and their production; the use of these substances as medicaments and for the production of antibacterially-active medicaments; as well as the manufacture of the compounds of formula I and their pharmaceutically acceptable salts and intermediates for their manufacture.

DETAILED DESCRIPTION OF THE INVENTION

The present invention relates to substituted 2,4-diaminopyrimidines of the formula

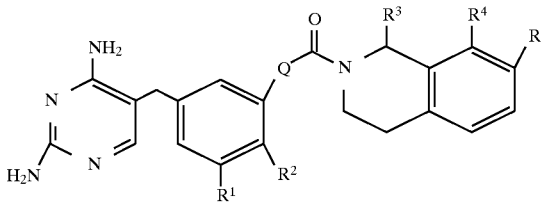

wherein $R^1$ is lower-alkoxy, $R^2$ is bromine, lower-alkoxy or hydroxy, $R^3$ is hydrogen, lower-alkyl, cycloalkyl, aryl, heterocyclyl, aralkyl, heterocyclyl-lower-alkyl or cyano, $R^4$ and $R^5$ each independently are hydrogen, lower-alkyl, lower-alkoxy, halogen, hydroxy, amino, di(lower alkyl) amino, cyano or nitro and Q is ethynylene or vinylene, as well as pharmaceutically usable salts thereof.

The term "lower" used here signifies a straight-chain or branched group with 1–6 C atoms. Examples of lower-alkyl are methyl, ethyl, n-propyl, isopropyl, n-butyl, sec.butyl, isobutyl, tert.butyl, n-pentyl and n-hexyl; examples of lower-alkoxy are correspondingly methoxy, ethoxy, n-propoxy, isopropoxy and t-butoxy. Under "cycloalkyl" there are to be understood cyclic alkyl groups with preferably 3–6 carbon atoms. The term "halogen" embraces fluorine, chlorine, bromine and iodine.

The term "aryl" denotes 6-membered mono- or polynuclear aromatic groups with preferably 6–14 carbon atoms. Phenyl, naphthyl, anthryl and phenanthryl are examples. These groups can be substituted, for example, by phenyl; lower-alkyl (for example, methyl); $C_{3-6}$-cycloalkyl (for example, cyclopropyl); halogen (for example, chlorine); trifluoro-methyl; lower-alkoxy (for example, methoxy, n-butoxy); lower alkoxy-carbonyl (for example, methoxycarbonyl); hydroxy; di(lower alkyl) amino (for example, dimethylamino, diethylamino); cyano; carbamoyl, mono- or di-lower-alkylcarbamoyl; lower-alkylsulfanyl, for example, methylsulfanyl; lower-alkylsulfonyl, for example, methanesulphonyl; sulfamoyl, N-mono- or di-lower alkyl-sufamoyl.

"Heterocyclyl" denotes 5- or 6-membered, mono- or poly-nuclear groups with preferably 5–13 carbon atoms and 1–4 hetero-atoms, preferably N,O and/or S. Furyl, pyranyl, thienyl, pyrrolyl, pyrazolyl, imidazolyl, thiazolyl, tetrazolyl, oxazolyl, oxadiazolyl, isoxazolyl, thiazolyl, isothiazolyl, pyridyl, pyridazinyl, pyrimidinyl, pyrazinyl, triazinyl are examples. These groups can also be linked with a fused ring, preferably a phenyl ring, such as benzopyranyl, benzofuranyl, indolyl and quinolinyl. The heterocyclyl groups can also be further substituted, for example as described above for the aryl groups. Preferred heterocyclyl groups are morpholin-4-yl, 4-methyl-piperazin-1-yl, imidazol-1-yl and [1,2,4]triazol-1-yl and tetrazolyl; and preferred heterocyclylalkyl groups are morpholin-4-ylmethyl, 4-methyl-piperazin-1-ylmethyl, imidazol-1-ylmethyl and [1,2,4]triazol-1-ylmethyl, and (cycloalkyl)amino.

Q is preferably vinylene.

Preferred compounds of formula I are those in which $R^1$ and $R^2$ are lower-alkoxy, especially methoxy; $R^3$ is substituted phenyl, or pyridyl, especially 2- or 3-pyridyl or substituted pyridyl, or thienyl; $R^4$ is hydrogen; and $R^5$ is hydrogen or lower-alkoxy, especially methoxy. The compounds of formula I in which $R^3$ is not hydrogen can be present in racemic form or as the R- or S-enantiomer. Examples of preferred compounds of formula I are:

(E)-(R)-3-[5-(2,4-Diamino-pyrimidin-5-ylmethyl)-2,3-dimethoxy-phenyl]-1-(1-pyridin-2-yl-3,4-dihydro-1H-isoquinolin-2-yl)-propenone, (Example 1);

(E)-(RS)-3-[5-(2,4-diamino-pyrimidin-5-ylmethyl)-2,3-dimethoxy-phenyl]-1-(1-pyridin-2-yl-3,4-dihydro-1H-isoquinolin-2-yl)-propenone, (Example 3);

(E)-(RS)-3-[5-(2,4-diamino-pyrimidin-5-ylmethyl)-2,3-dimethoxy-phenyl]-1-(7-methoxy-1-pyridin-2-yl-3,4-dihydro-1H-isoquinolin-2-yl)-propenone, (Example 8);

(E)-(RS)-3-[5-(2,4-diamino-pyrimidin-5-ylmethyl)-2,3-dimethoxy-phenyl]-1-[1-(4-methyl-phenyl)-3,4-dihydro-1H-isoquinolin-2-yl]-propenone, (Example 16);

(E)-(RS)-3-[5-(2,4-diamino-pyrimidin-5-ylmethyl)-2,3-dimethoxy-phenyl]-1-[1-(4-hydroxy-phenyl)-3,4-dihydro-1H-isoquinolin-2-yl]-propenone, (Example 21);

(E)-(RS)-1-(1-cyclopropyl-3,4-dihydro-1H-isoquinolin-2-yl)-3-[5-(2,4-diamino-pyrimidin-5-ylmethyl)-2,3-dimethoxyphenyl]-propenone, (Example 22);

(E)-(RS)-4-[2-[3-[5-(2,4-diamino-pyrimidin-5-yl)-2,3-dimethoxy-phenyl]-acryloyl]-1,2,3,4-tetrahydro-isoquinolin-1-yl]-benzonitrile, (Example 23);

(E)-(RS)-3-[5-(2,4-diamino-pyrimidin-5-ylmethyl)-2,3-dimethoxy-phenyl]-1-(1-thiophen-2-yl-3,4-dihydro-1H-isoquinolin-2-yl)-propenone, (Example 27);

(E)-(RS)-3-[5-(2,4-diamino-pyrimidin-5-ylmethyl)-2,3-dimethoxy-phenyl]-1-[1-(6-methyl-pyridin-3-yl)-3,4-dihydro-1H-isoquinolin-2-yl]-propenone, (Example 32);

(E)-(RS)-1-[1-(5-chloro-pyridin-2-yl)-3,4-dihydro-1H-isoquinolin-2-yl]-3-[5-(2,4-diamino-pyrimidin-5-ylmethyl)-2,3-dimethoxy-phenyl]-propenone, (Example 34);

(E)-(RS)-1-[1-(6-chloro-pyridin-3-yl)-3,4-dihydro-1H-isoquinolin-2-yl]-3-[5-(2,4-diamino-pyrimidin-5-ylmethyl)-2,3-dimethoxy-phenyl]-propenone, (Example 36);

(E)-(RS)-5-[2-[3-[5-(2,4-diamino-pyrimidin-5-ylmethyl)-2,3-dimethoxy-phenyl]-acryloyl]-1,2,3,4-tetrahydro-isoquinolin-1-yl]-pyridin-2-carboxamide, (Example 39);

(E)-(RS)-3-[5-(2,4-diamino-pyrimidin-5-ylmethyl)-2,3-dimethoxy-phenyl]-1-[1-(4-methanesulphonyl-phenyl)-3,4-dihydro-1H-isoquinolin-2-yl]-propenone, (Example 40);

(E)-(RS)-3-[5-(2,4-diamino-pyrimidin-5-ylmethyl)-2,3-dimethoxy-phenyl]-1-[1-(4-dimethylamino-pyridin-2-yl)-3,4-dihydro-1H-isoquinolin-2-yl]-propenone, (Example 44);

(E)-(RS)-4-(2-{3-[5-(2,4-diamino-pyrimidin-5-ylmethyl)-2,3-dimethoxy-phenyl]-acryloyl}-1,2,3,4-tetrahydro-isoquinolin-1-yl)-benzamide, (Example 49);

(E)-(RS)-3-[5-(2,4-diamino-pyrimidin-5-ylmethyl)-2,3-dimethoxy-phenyl]-1-[1-(4-methylsulphanyl-phenyl)-3,4-dihydro-1H-isoquinolin-2-yl]-propenone, (Example 55); and (E)-(RS)-3-[5-(2,4-diamino-pyrimidin-5-ylmethyl)-2,3-dimethoxy-phenyl]-1-[1-(2,5-dimethyl-2H-pyrazol-3-yl)-3,4-dihydro-1H-isoquinolin-2-yl]-propenone, (Example 71); as well as pharmaceutically usable salts of these compounds.

The compounds of formula I form pharmaceutically acceptable acid addition salts with organic and inorganic acids. Examples of acid addition salts of compounds of formula I are salts with mineral acids, for example hydrohalic acids such as hydrochloric acid, hydrogen bromide and hydrogen iodide, sulfuric acid, nitric acid, phosphoric acid and the like, salts with organic sulfonic acids, for example with alkyl- and arylsulfonic acids such as methanesulfonic acid, p-toluenesulfonic acid, benzenesulfonic acid and the like, as well as salts with organic carboxylic acids, for example with acetic acid, tartaric acid, maleic acid, citric acid, benzoic acid, salicylic acid, ascorbic acid and the like.

The compounds of formula I and their pharmaceutically acceptable salts can be manufactured in accordance with the invention by (a) reacting a compound of the formula

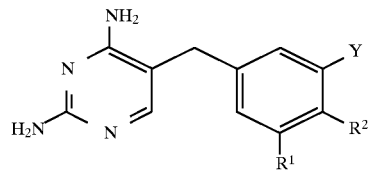

II with a compound of the formula

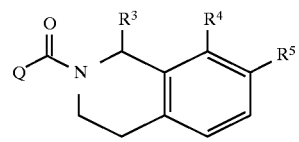

III in which $R^1$–$R^5$ and Q have the above significance and Y represents a leaving group, or b) if desired, functionally modifying reactive groups present in the reaction product, or c) converting a compound of formula I into a pharmaceutically acceptable salt.

In order to manufacture end products of formula I in accordance with process variant a) of the process in accordance with the invention a so-called "Heck reaction" is carried out by, for example, reacting a starting material of formula II in which Y represents bromine, iodine, methanesulphonyloxy, trifluoro-methanesulphonyloxy, benzenesulphonyloxy or p-toluene-sulphonyloxy with a compound of formula III. Preferably, an inert organic solvent, for example, dioxan, tetrahydrofuran, N,N-dimethylacetamide or N,N-dimethylformamide, is used. The reaction is preferably effected in the presence of a base, such as, an alkali metal carbonate, for example, potassium carbonate, or a tertiary amine, for example, in a tri(lower alkyl)amine such as triethylamine or tri-n-butylamine, and together with a catalyst, preferably a palladium complex such as palladium (II) acetate, bis(triphenylphosphine)palladium(II) dichloride, bis(triphenylphosphine)palladium(II) diacetate, tetrakistriphenylphosphine-palladium, or copper(I) iodide and triphenylphosphine or tri-o-tolylphosphine, optionally with the addition of a phase transfer catalyst such as a tetraalkylammonium salt, for example, tetramethylammonium chloride. The temperature of the "Heck reaction" preferably lies in the region between about 40° C. and the boiling point of the reaction mixture.

If desired, reactive groups present in the product of formula I can be functionally modified in accordance with variant b) of the process in accordance with the invention. For example, groups $R^3$ such as cyano or cyanophenyl can be converted into groups $R^3$ such as tetrazolyl or tetrazolylphenyl. This reaction is effected, for example, by treatment with sodium azide in N,N-dimethyl-formamide in the presence of ammonium chloride. The temperature preferably lies between 60° C. and 120° C., especially at 90° C.

The manufacture of the salts of the compounds of formula I in accordance with variant c) can be effected in a known manner for example, by reacting a compound of formula I with an organic or inorganic acid, conveniently in a solvent such as acetone, ethanol, methanol or water.

The compounds of formula III can be obtained in accordance with the invention by reacting a compound of the formula

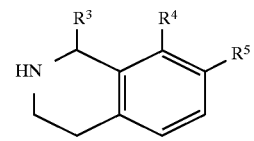

IV in which $R^3$–$R^5$ have the above significance, with a reactive derivative of acrylic acid or of propiolic acid.

Examples of reactive derivatives of acrylic acid or propiolic acid are the acid halides, especially the chloride, reactive amides such as the imidazolide and mixed anhydrides. The acylation in accordance with the invention can be carried out in an inert solvent, for example, a hydrocarbon such as benzene or toluene, a chlorinated hydrocarbon such as chloroform or methylene chloride or an ether such as dioxan or tetrahydrofuran, in the presence of a base, for example, an amine such as pyridine or triethylamine (which can simultaneously serve as the solvent). The reaction temperature is not critical. The reaction is conveniently performed at temperatures between 0° C. and 50° C., especially at 0° C. to 30° C.

The compounds of formula III (Q=ethynylene) can be prepared, for example, according to the following Reaction Scheme:

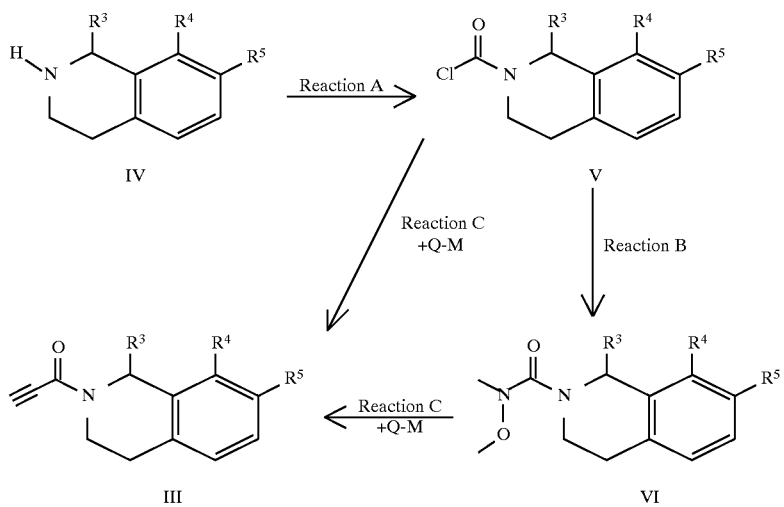

wherein Q is ethynylene and, $R^3$, $R^4$ and $R^5$ have the above significance and M signifies —Li, —Na, —MgBr, —MgCl, or —MgI.

Reaction A

This reaction can be carried out according to methods which are known per se and will be familiar to any person skilled in the art. It is preferably carried out by treatment with phosgene or with a phosgene substitute such as trichloromethyl chloroformate (diphosgene) or bis (trichloromethyl) carbonate (triphosgene). The chloroacylation in accordance with the invention can be carried out in an inert solvent, for example, a hydrocarbon such as benzene or toluene, a chlorinated hydrocarbon such as chloroform, methylene chloride or dichloroethane, or an ether such as dioxan or tetrahydrofuran, in the presence of a base, for example, an amine such as pyridine or triethylamine (which can simultaneously serve as the solvent). The reaction is carried out at temperatures between −20° C. and 110° C., especially at 0° C. to 50° C.

Reaction B

This reaction is the production of a substituted urea derivative VI. It can be carried out according to methods known per se by reacting a carbamoyl chloride V with an amine of the formula $HNR^6R^7$ wherein $R^6$ and $R^7$ are lower alkyl or lower alkoxy, preferably methyl and methoxy, respectively; or a salt of this amine wherein $R^6$ and $R^7$ are lower alkyl or lower alkoxy, preferably methyl and methoxy, respectively. A chlorinated lower hydrocarbon such as chloroform or methylene chloride is preferably used as the solvent. The reaction is preferably carried out in the presence of an organic base such as pyridine, triethylamine or 4-dimethylaminopyridine in a temperature range of −10° C. to 60° C.

Reaction C

This reaction can be carried out according to methods which are known per se and which will be familiar to any person skilled in the art. It is preferably carried out in a temperature range of −80° C. to 20° C. The symbol M preferably signifies —MgBr. An open-chain or cyclic ether such as diethyl ether, dimethoxyethane or tetrahydrofuran is preferably used as the solvent.

The starting materials of formulas II and IV are known or can be prepared as described in the Examples or in analogy thereto.

As mentioned earlier, the compounds of formula I and their pharmaceutically acceptable salts possess valuable antibacterial properties. They are active against a large number of pathogenic microorganisms such as, for example, *Staphylococcus aureus, Pneumocystis carinii* and the like by virtue of their activity in inhibiting bacterial dihydrofolate reductase (DHFR). The inhibition of this enzyme was taken as a measurement of the antibacterial activity. It is determined by the method of D. P. Baccanari and S. S. Joyner (Biochemistry 20, 1710 (1981)); see also P. G. Hartman et al., FEBS Letters 242, 157 (1988). The $IC_{50}$ values (concentration at which the enzyme is inhibited by 50%) are determined by means of a graph.

The following Table contains inhibitory concentrations obtained for representative members of the class of compound defined by formula I and determined in the above test. The $IC_{50}$ values ($\mu M$) against the purified DHFR of the reference strain *S. aureus* ATCC 25923 as well as against the purified DHFR of the multiresistant strain *S. aureus* 157/4696 are given. The third column shows the $IC_{50}$ values ($\mu M$) against the purified DHFR of the opportunistic pathogen *P. carinii*. The inhibition constants of trimethoprim are also given as a comparison.

| Examples | S. aureus ATCC 25923 | S. aureus 157/4696 | P. carinii |
|---|---|---|---|
| Trimethoprim | 0.0340 | 16.0000 | 43.00 |
| 1 | 0.0050 | 0.0080 | 8.00 |
| 3 | 0.0090 | 0.0095 | 17.00 |
| 8 | 0.0050 | 0.0090 | 5.00 |
| 16 | 0.0002 | 0.0048 | 0.33 |

-continued

| Examples | S. aureus ATCC 25923 | S. aureus 157/4696 | P. carinii |
|---|---|---|---|
| 21 | 0.0055 | 0.0130 | 0.38 |
| 27 | 0.0016 | 0.0018 | 3.80 |
| 32 | 0.0018 | 0.0013 | 10.00 |
| 34 | 0.0024 | 0.0017 | 10.00 |
| 23 | 0.0005 | 0.0009 | 10.00 |
| 36 | 0.0008 | 0.0030 | 6.2 |
| 39 | 0.0012 | 0.0018 | 30.00 |
| 40 | 0.0007 | 0.0012 | 0.55 |

The products in accordance with the invention can be used as medicaments, for example, in the form of pharmaceutical preparations for enteral or parenteral administration. For example, the products in accordance with the invention can be administered perorally, for example, in the form of tablets, coated tablets, dragées, hard and soft gelatin capsules, solutions, emulsions or suspensions, rectally, for example, in the form of suppositories, or parenterally, for example, in the form of injection solutions.

The production of the pharmaceutical preparations can be effected in a manner which will be familiar to any person skilled in the art by bringing the substances in accordance with the invention, optionally in combination with other therapeutically valuable substances, into a galenical administration form together with suitable, non-toxic, inert, therapeutically compatible solid or liquid carrier materials and, if desired, the usual pharmaceutical adjuvants.

Both inorganic and organic carrier materials are suitable as such carrier materials. Thus, for example, lactose, corn starch or derivatives thereof, talc, stearic acid or its salts can be used as carrier materials for tablets, coated tablets, dragées and hard gelatin capsules. Suitable carriers for soft gelatin capsules are, for example, vegetable oils, waxes, fats and semi-solid and liquid polyols (depending on the nature of the active ingredient no carriers are, however, required in the case of soft gelatin capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

The usual preservatives, solubilizers, stabilizers, wetting agents, emulsifiers, sweeteners, colorants, flavorants, salts for varying the osmotic pressure, buffers, masking agents and antioxidants come into consideration as pharmaceutical adjuvants. For parenteral administration the compounds of formula I and, respectively, their salts are preferably provided as lyophilizates or dry powders for dilution with usual carriers such as water or isotonic saline.

As mentioned earlier, the compounds of formula I and their salts have antibacterial activity. They inhibit bacterial dihydrofolate reductase and potentiate the antibacterial activity of sulfonamides such as, for example, sulfisoxazole, sulfadimethoxine, sulfamethoxazole, 4-sulphanilamido-5,6-dimethoxypyrimidine, 2-sulphanilamido-4,5-dimethylpyrimidine or sulfaquinoxaline, sulfadiazine, sulfamonomethoxine, 2-sulphanilamido-4,5-dimethylisoxazole and other inhibitors of enzymes which are involved in folic acid biosynthesis, such as, for example, pteridine derivatives.

Oral, rectal and parenteral administration come into consideration in human medicine for such combinations of one or more compounds of formula I in accordance with the invention with sulfonamides. The ratio of a compound of formula I to a sulfonamide can vary within a broad range of from 1:40 (parts by weight) to 1:1 (parts by weight); preferred ratios are 1:10 to 1:2. Thus, for example, a tablet can contain 80 mg of a compound of formula I in accordance with the invention and 400 mg of sulfamethoxazole, a tablet for children can contain 20 mg of a compound of formula I in accordance with the invention and 100 mg of sulfamethoxazole; syrup (per 5 ml) can contain 40 mg of a compound of formula I and 200 mg of sulfamethoxazole. A daily dosage of about 0.2 g to about 2 g of a compound of formula 1, when administered alone or in combination with sulfonamides, in accordance with the invention comes into consideration for adults.

The compounds of formula I are characterized by a high antibacterial activity and a pronounced synergistic effect in combination with sulfonamides and are well tolerated.

The following Examples illustrate the invention in more detail.

EXAMPLE 1

7.74 g of (R)-1-(1-pyridin-2-yl-3,4-dihydro-1H-isoquinolin-2-yl)-propenone in 30 ml of N,N-dimethylacetamide were treated with 9.65 g of 5-(3-iodo-4,5-dimethoxy-benzyl)-pyrimidin-2,4-diamine, 112 mg of palladium(II) acetate, 608 mg of tri-o-tolylphosphine as well as 4.3 ml of triethylamine and stirred at 120° C. for 25 min. 150 ml of a 10% sodium bicarbonate solution were added dropwise while stirring to the reaction mixture which had been cooled to room temperature. Thereafter, the reaction mixture was treated with 100 ml of dichloromethane and stirred for a further 10 min. The phases were separated and the aqueous phase was extracted with 30 ml of dichloromethane. From the combined dichloromethane phases there were obtained, after drying over sodium sulfate and concentrated, 19 g of a pale, orange foam which was subjected to chromatography on 250 g of silica gel using the eluent dichloromethane-methanol-25% ammonia. The pure fractions were combined and concentrated. Recrystallization of the yellowish residue (10.85 g) from acetonitrile/ethanol yielded 9.54 g of (E)-(R)-3-[5-(2,4-diamino-pyrimidin-5-ylmethyl)-2,3-dimethoxy-phenyl]-1-(1-pyridin-2-yl-3,4-dihydro-1H-isoquinolin-2-yl)-propenone as a beige product, m.p 136°–140° C.

The following compounds were prepared in analogy to Example 1:

EXAMPLES 2–70

2. (E)-3-[5-(2,4-Diamino-pyrimidin-5-ylmethyl)-2,3-dimethoxy-phenyl]-1-(3,4-dihydro-1H-isoquinolin-2-yl)-propenone, m.p. 110°–112° C., dec. (ethanol).
3. (E)-(RS)-3-[5-(2,4-Diamino-pyrimidin-5-ylmethyl)-2,3-dimethoxy-phenyl]-1-(1-pyridin-2-yl-3,4-dihydro-1H-isoquinolin-2-yl)-propenone, m.p. 193°–196° C. (acetonitrile).
4. (E)-1-(7-Chloro-3,4-dihydro-1H-isoquinolin-2-yl)-3-[5-2,4-diamino-pyrimidin-5-ylmethyl)-2,3-dimethoxy-phenyl]-propenone, m.p. 157°–160° C.
5. (E)-(RS)-3-[5-(2,4-Diamino-pyrimidin-5-ylmethyl)-2,3-dimethoxy-phenyl]-1-(1-phenyl-3,4-dihydro-1H-isoquinolin-2-yl)-propenone, m.p. 155°–160° C. (acetonitrile).
6. (E)-(RS)-3-[5-(2,4-Diamino-pyrimidin-5-ylmethyl)-2,3-dimethoxy-phenyl]-1-(1-pyridin-4-yl-3,4-dihydro-1H-isoquinolin-2-yl)-propenone, m.p. 125°–128° C. (water).
7. (E)-(RS)-3-[5-(2,4-Diamino-pyrimidin-5-ylmethyl)-2,3-dimethoxy-phenyl]-1-(1-pyridin-3-yl-3,4-dihydro-1H-isoquinolin-2-yl)-propenone, m.p. 229° C. (ethanol).

8. (E)-(RS)-3-[5-(2,4-Diamino-pyrimidin-5-ylmethyl)-2,3-dimethoxy-phenyl]-1-(7-methoxy-1-pyridin-2-yl-3,4-dihydro-1H-isoquinolin-2-yl)-propenone, m.p. 167°–169° C.

9. 3-[5-(2,4-Diamino-pyrimidin-5-ylmethyl)-2,3-dimethoxy-phenyl]-1-(3,4-dihydro-1H-isoquinolin-2-yl)-propynone, m.p. 113°–116° C. (chloroform/hexane).

10. (E)-(RS)-3-[5-(2,4-Diamino-pyrimidin-5-ylmethyl)-2,3-dimethoxy-phenyl]-1-(1-pyrazin-2-yl-3,4-dihydro-1H-isoquinolin-2-yl)-propenone, m.p. 210°–214° C. (ethanol).

11. (E)-(RS)-1-(7-Chloro-1-pyridin-2-yl-3,4-dihydro-1H-isoquinolin-2-yl)-3-[5-(2,4-diamino-pyrimidin-5-ylmethyl)-2,3-dimethoxy-phenyl]-propenone, m.p. 195°–196° C. (ethanol).

12. (E)-(RS)-3-[5-(2,4-Diamino-pyrimidin-5-ylmethyl)-2,3-dimethoxy-phenyl]-1-(7-methyl-1-pyridin-2-yl-3,4-dihydro-1H-isoquinolin-2-yl)-propenone, m.p. 185°–187° C. (acetonitrile).

13. (E)-(RS)-1-[1-(4-Chloro-phenyl)-3,4-dihydro-1H-isoquinolin-2-yl]-3-[5-(2,4-diamino-pyrimidin-5-ylmethyl)-2,3-dimethoxy-phenyl]-propenone, m.p. 148°–150° C. (1,2-dimethoxy-ethane).

14. (E)-(RS)-1-(1-Cyclohexyl-3,4-dihydro-1H-isoquinolin-2-yl)-3-[5-(2,4-diamino-pyrimidin-5-ylmethyl)-2,3-dimethoxy-phenyl]-propenone, m.p. 203° C. (ethanol).

15. (E)-(RS)-3-[5-(2,4-Diamino-pyrimidin-5-ylmethyl)-2,3-dimethoxy-phenyl]-1-(1-pyrimidin-5-yl-3,4-dihydro-1H-isoquinolin-2-yl)-propenone hydrochloride (1:1.75), m.p. 155° C., dec. (ethanol).

16. (E)-(RS)-3-[5-(2,4-Diamino-pyrimidin-5-ylmethyl)-2,3-dimethoxy-phenyl]-1-[1-(4-methyl-phenyl)-3,4-dihydro-1H-isoquinolin-2-yl]-propenone, m.p. 155°–157° C. (acetonitrile).

17. (E)-(RS)-3-[5-(2,4-Diamino-pyrimidin-5-ylmethyl)-2,3-dimethoxy-phenyl]-1-(1-pyrimidin-4-yl-3,4-dihydro-1H-isoquinolin-2-yl)-propenone, m.p. 97° C., dec. (ethanol).

18. (E)-(RS)-1-(1-Benzyl-3,4-dihydro-1H-isoquinolin-2-yl)-3-[5-(2,4-diamino-pyrimidin-5-ylmethyl)-2,3-dimethoxy-phenyl]-propenone, m.p. 107°–120° C.

19. (E)-(RS)-3-[5-(2,4-Diamino-pyrimidin-5-ylmethyl)-2,3-dimethoxy-phenyl]-1-(1-isobutyl-3,4-dihydro-1H-isoquinolin-2-yl)-propenone, m.p. 107° C. (ethanol).

20. (E)-(RS)-3-[5-(2,4-Diamino-pyrimidin-5-ylmethyl)-2,3-dimethoxy-phenyl]-1-[1-(4-methoxy-phenyl)-3,4-dihydro-1H-isoquinolin-2-yl]-propenone, m.p. 191°–194° C. (acetonitrile).

21. (E)-(RS)-3-[5-(2,4-Diamino-pyrimidin-5-ylmethyl)-2,3-dimethoxy-phenyl]-1-[1-(4-hydroxy-phenyl)-3,4-dihydro-1H-isoquinolin-2-yl]-propenone, m.p. 170°–172° C. (acetonitrile).

22. (E)-(RS)-1-(1-Cyclopropyl-3,4-dihydro-1H-isoquinolin-2-yl)-3-[5-(2,4-diamino-pyrimidin-5-ylmethyl)-2,3-dimethoxy-phenyl]-propenone, m.p. 115°–125° C. (acetonitrile).

23. (E)-(RS)-4-[2-[3-[5-(2,4-Diamino-pyrimidin-5-yl)-2,3-dimethoxy-phenyl]-acryloyl]1,2,3,4-tetrahydro-isoquinolin-1-yl]-benzonitrile, m.p. 158°–161° C. (acetonitrile).

24. (E)-(RS)-3-[5-(2,4-Diamino-pyrimidin-5-ylmethyl)-3-dimethoxy-phenyl]-1-[1-(4-dimethylamino-phenyl)-3,4-dihydro-1H-isoquinolin-2-yl]-propenone, m.p. 157°–160° C. (acetonitrile).

25. (E)-(RS)-3-[5-(2,4-Diamino-pyrimidin-5-ylmethyl)-2,3-dimethoxy-phenyl]-1-(1-pyridazin-3-yl-3,4-dihydro-1H-isoquinolin-2-yl)-propenone, m.p. 128° C., dec. (ethanol/diethyl ether).

26. (E)-(RS)-3-[5-(2,4-Diamino-pyrimidin-5-ylmethyl)-2,3-dimethoxy-phenyl]-1-(1-pyridazin-4-yl-3,4-dihydro-1H-isoquinolin-2-yl)-propenone, m.p. 122° C., dec. (methanol/acetonitrile).

27. (E)-(RS)-3-[5-(2,4-Diamino-pyrimidin-5-ylmethyl)-2,3-dimethoxy-phenyl]-1-(1-thiophen-2-yl-3,4-dihydro-1H-isoquinolin-2-yl)-propenone, m.p. 116° C., dec. (ethanol/methanol).

28. (E)-(RS)-2-[3-[5-(2,4-Diamino-pyrimidin-5-ylmethyl)-2,3-dimethoxy-phenyl]-acryloyl]-1,2,3,4-tetrahydro-isoquinoline-1-carbonitrile, m.p. 226° C., dec. (methylene chloride/tert.-butyl methyl ether (t-BuOMe)).

29. (E)-(RS)-3-[5-(2,4-Diamino-pyrimidin-5-ylmethyl)-2,3-dimethoxy-phenyl]-1-[1-(4-trifluoromethyl-phenyl)-3,4-dihydro-1H-isoquinolin-2-yl]-propenone, m.p. 155°–157° C. (acetonitrile).

30. (E)-(RS)-3-[5-(2,4-Diamino-pyrimidin-5-ylmethyl)-2,3-dimethoxy-phenyl]-1-[1-(6-hydroxy-pyridin-3-yl)-3,4-dihydro-1H-isoquinolin-2-yl]-propenone trifluoroacetate (1:1), MS (ISP): 539.4 (M+H)$^+$.

31. Ethyl (E)-(RS)-4-[2-[3-[5-(2,4-diamino-pyrimidin-5-ylmethyl)-2,3-dimethoxy-phenyl]-acryloyl]-1,2,3,4-tetrahydro-isoquinolin-1-yl]-benzoate, m.p. 125°–130° C. (acetonitrile).

32. (E)-(RS)-3-[5-(2,4-Diamino-pyrimidin-5-ylmethyl)-2,3-dimethoxy-phenyl]-1-[1-(6-methyl-pyridin-3-yl)-3,4-dihydro-1H-isoquinolin-2-yl]-propenone, m.p. 205° C. (acetonitrile).

33. (E)-(RS)-1-[1-(4-Chloro-pyridin-2-yl)-3,4-dihydro-1H-isoquinolin-2-yl]-3-[5-(2,4-diamino-pyrimidin-5-ylmethyl)-2,3-dimethoxy-phenyl]-propenone, m.p. 141°–145° C. (acetonitrile).

34. (E)-(RS)-1-[1-(5-Chloro-pyridin-2-yl)-3,4-dihydro-1H-isoquinolin-2-yl]-3-[5-(2,4-diamino-pyrimidin-5-ylmethyl)-2,3-dimethoxy-phenyl]-propenone, m.p. 130°–132° C. (acetonitrile).

35. (E)-(RS)-3-[5-(2,4-Diamino-pyrimidin-5-ylmethyl)-2,3-dimethoxy-phenyl]-1-[1-(6-dimethylamino-pyridin-3-yl)-3,4-dihydro-1H-isoquinolin-2-yl]-propenone, m.p. 155°–156° C. (acetonitrile).

36. (E)-(RS)-1-[1-(6-Chloro-pyridin-3-yl)-3,4-dihydro-1H-isoquinolin-2-yl]-3-[5-(2,4-diamino-pyrimidin-5-ylmethyl)-2,3-dimethoxy-phenyl]-propenone, m.p. 157° C. (ethanol).

37. (E)-(RS)-3-[5-(2,4-Diamino-pyrimidin-5-ylmethyl)-2-hydroxy-3-methoxy-phenyl]-1-(1-pyridin-2-yl-3,4-dihydro-1H-isoquinolin-2-yl)-propenone, m.p. 145°–155° C. (acetonitrile/ethanol).

38. (E)-(RS)-3-[5-(2,4-Diamino-pyrimidin-5-ylmethyl)-2,3-dimethoxy-phenyl]-1-[1-(4-diethylaminomethyl-phenyl)-3,4-dihydro-1H-isoquinolin-2-yl]-propenone, m.p. 112°–114° C. (acetonitrile).

39. (E)-(R,S)-5-[2-[3-[5-(2,4-Diamino-pyrimidin-5-ylmethyl)-2,3-dimethoxy-phenyl]-acryloyl]-1,2,3,4-tetrahydro-isoquinolin-1-yl]-pyridine-2-carboxamide, m.p. 162°–170° C. (ethanol).

40. (E)-(R,S)-3-[5-(2,4-Diamino-pyrimidin-5-ylmethyl)-2,3-dimethoxy-phenyl]-1-[1-(4-methanesulphonyl-phenyl)-3,4-dihydro-1H-isoquinolin-2-yl]-propenone, m.p. 140°–150° C. (acetonitrile).

41. (E)-(RS)-3-[5-(2,4-Diamino-pyrimidin-5-ylmethyl)-2,3-dimethoxy-phenyl]-1-[1-(4-methoxy-pyridin-2-yl)-3,4-dihydro-1H-isoquinolin-2-yl]-propenone, m.p. 232°–235° C. (ethanol/acetonitrile).

42. (E)-(RS)-5-(2-{3-[5-(2,4-Diamino-pyrimidin-5-ylmethyl)-2,3-dimethoxy-phenyl]-acryloyl}-1,2,3,4-tetrahydro-isoquinolin-1-yl)-pyridine-2-carboxamide, m.p. 162°–170° C. (ethanol).

43. (E)-(RS)-3-[5-(2,4-Diamino-pyrimidin-5-ylmethyl)-2,3-dimethoxy-phenyl]-1-[1-(4-methanesulphonyl-phenyl)-3,4-dihydro-1H-isoquinolin-2-yl]-propenone, m.p. 140°–150° C. (acetonitrile).

44. (E)-(RS)-3-[5-(2,4-Diamino-pyrimidin-5-ylmethyl)-2,3-dimethoxy-phenyl]-1-[1-(4-dimethylamino-pyridin-2-yl)-3,4-dihydro-1H-isoquinolin-2-yl]-propenone, m.p. 215°–218° C. (acetonitrile).

45. (E)-(RS)-3-[5-(2,4-Diamino-pyrimidin-5-ylmethyl)-2,3-dimethoxy-phenyl]-1-[1-(6-morpholin-4-yl-pyridin-3-yl)-3,4-dihydro-1H-isoquinolin-2-yl]-propenone, m.p. 137°–145° C. (acetonitrile).

46. (E)-(RS)-3-[5-(2,4-Diamino-pyrimidin-5-ylmethyl)-2,3-dimethoxy-phenyl]-1-[1-(4-fluoro-phenyl)-3,4-dihydro-1H-isoquinolin-2-yl]-propenone, m.p. 126°–130° C. (acetonitrile).

47. (E)-(RS)-3-[5-(2,4-Diamino-pyrimidin-5-ylmethyl)-2,3-dimethoxy-phenyl]-1-{1-[6-(4-methyl-piperazin-1-yl)-pyridin-3-yl]-3,4-dihydro-1H-isoquinolin-2-yl}-propenone, m.p. 133°–138° C. (acetonitrile).

48. (E)-(RS)-3-[5-(2,4-Diamino-pyrimidin-5-ylmethyl)-2,3-dimethoxy-phenyl]-1-[1-(4-morpholin-4-ylmethyl-phenyl)-3,4-dihydro-1H-isoquinolin-2-yl]-propenone, m.p. 118°–125° C. (acetonitrile).

49. (E)-(RS)-4-(2-{3-[5-(2,4-Diamino-pyrimidin-5-ylmethyl)-2,3-dimethoxy-phenyl]-acryloyl}-1,2,3,4-tetrahydro-isoquinolin-1-yl)-benzamide, m.p. 153°–165° C. (ethanol).

50. (E)-(RS)-3-[5-(2,4-Diamino-pyrimidin-5-ylmethyl)-2,3-dimethoxy-phenyl]-1-{1-[4-(4-methyl-piperazin-1-ylmethyl)-phenyl]-3,4-dihydro-1H-isoquinolin-2-yl}-propenone, m.p. 235°–238° C. (ethanol).

51. (E)-(RS)-3-[5-(2,4-Diamino-pyrimidin-5-ylmethyl)-2,3-dimethoxy-phenyl]-1-[1-(4-imidazol-1-yl-phenyl)-3,4-dihydro-1H-isoquinolin-2-yl]-propenone, m.p. 155°–159° C. (acetonitrile).

52. (E)-(RS)-3-[5-(2,4-Diamino-pyrimidin-5-ylmethyl)-2,3-dimethoxy-phenyl]-1-[1-(4-imidazol-1-ylmethyl-phenyl)-3,4-dihydro-1H-isoquinolin-2-yl]-propenone, m.p. 213.5°–214.5° C. (isopropanol).

53. (E)-(RS)-3-[5-(2,4-Diamino-pyrimidin-5-ylmethyl)-2,3-dimethoxy-phenyl]-1-[1-(4-[1,2,4]triazol-1-yl-phenyl)-3,4-dihydro-1H-isoquinolin-2-yl]-propenone, m.p. 156°–162° C. (ethanol/acetonitrile).

54. (E)-(RS)-3-[5-(Z,4-Diamino-pyrimidin-5-ylmethyl)-2,3-dimethoxy-phenyl]-1-[1-(4-[1,2,4]triazol-1-ylmethyl-phenyl)-3,4-dihydro-1H-isoquinolin-2-yl]-propenone, m.p. 190°–194° C. (acetonitrile).

55. (E)-(RS)-3-[5-(2,4-Diamino-pyrimidin-5-ylmethyl)-2,3-dimethoxy-phenyl]-1-[1-(4-methylsulphanyl-phenyl)-3,4-dihydro-1H-isoquinolin-2-yl]-propenone, m.p. 220° C. (ethanol).

56. (E)-(RS)-3-[5-(2,4-Diamino-pyrimidin-5-ylmethyl)-2,3-dimethoxy-phenyl]-1-[1-(3-methanesulfonyl-phenyl)-3,4-dihydro-1H-isoquinolin-2-yl]-propenone, m.p. 230° C. (ethanol/acetonitrile).

57. (E)-(RS) 3-[5-(2,4-Diamino-pyrimidin-5-ylmethyl)-2,3-dimethoxy-phenyl]-1-[1-(6-methylsulphanyl-pyridin-3-yl)-3,4-dihydro-1H-isoquinolin-2-yl]-propenone, m.p. 165° C. (acetonitrile).

58. (E)-(RS)-3-[5-(2,4-Diamino-pyrimidin-5-ylmethyl)-2,3-dimethoxy-phenyl]-1-(1-{6-[(2-hydroxy-ethyl)-methyl-amino]-pyridin-3-yl}-3,4-dihydro-1H-isoquinolin-2-yl)-propenone, m.p. 156° C. (ethanol/acetonitrile).

59. (E)-(RS)-3-[5-(2,4-Diamino-pyrimidin-5-ylmethyl)-2,3-dimethoxy-phenyl]-1-(1-methyl-3,4-dihydro-1H-isoquinolin-2-yl)-propenone, m.p. 136°–137° C. (ethanol/acetonitrile).

60. (E)-(RS)-3-[5-(2,4-Diamino-pyrimidin-5-ylmethyl)-2,3-dimethoxy-phenyl]-1-[1-(4-hydroxymethyl-phenyl)-3,4-dihydro-1H-isoquinolin-2-yl]-propenone, m.p. 154° C. (ethanol).

61. (E)-(RS)-3-[5-(2,4-Diamino-pyrimidin-5-ylmethyl)-2,3-dimethoxy-phenyl]-1-(1-ethyl-3,4-dihydro-1H-isoquinolin-2-yl)-propenone, m.p. 133° C. (ethanol).

62. (E)-(RS)-3-[5-(2,4-Diamino-pyrimidin-5-ylmethyl)-2,3-dimethoxy-phenyl]-1-[1-(2-methyl-4-morpholin-4-ylmethyl-2H-pyrazol-3-yl)-3,4-dihydro-1H-isoquinolin-2-yl]-propenone, m.p. 133°–135° C. (ethanol).

63. (E)-(RS)-3-[5-(2,4-Diamino-pyrimidin-5-ylmethyl)-2,3-dimethoxy-phenyl]-1-[1-[1-methyl-5-(4-methyl-piperazin-1-ylmethyl)-1H-pyrazol-3-yl]-3,4-dihydro-1H-isoquinolin-2-yl]-propenone, m.p. >130° C. dec. (ethanol/tert.-butyl methyl ether).

64. (E)-(RS)-3-[5-(2,4-Diamino-pyrimidin-5-ylmethyl)-2,3-dimethoxy-phenyl]-1-[1-(1-methyl-4-morpholin-4-ylmethyl-1H-pyrazol-3-yl)-3,4-dihydro-1H-isoquinolin-2-yl]-propenone, m.p. >130° C. dec. (acetonitrile).

65. (E)-(RS)-3-[5-(2,4-Diamino-pyrimidin-5-ylmethyl)-2,3-dimethoxy-phenyl]-1-[1-(2-methyl-5-morpholin-4-ylmethyl-2H-pyrazol-3-yl)-3,4-dihydro-1H-isoquinolin-2-yl]-propenone, beige foam, MS (ISP): 625.4 (M+H)⁺.

66. (E)-(RS)-2-[5-[2-[3-[5-(2,4-Diamino-pyrimidin-5-ylmethyl)-2,3-dimethoxyphenyl]-acryloyl]-1,2,3,4-tetrahydro-isoquinolin-1-yl]-1-methyl-1H-pyrazol-3-yl]-acetamide, beige foam, MS (ISP): 583.3 (M+H)⁺.

67. (E)-(RS)-3-[5-(2,4-Diamino-pyrimidin-5-ylmethyl)-2,3-dimethoxy-phenyl)-1-[1-(1-methyl-5-morpholin-4-ylmethyl-1H-pyrazol-3-yl)-3,4-dihydro-1H-isoquinolin-2-yl]-propenone, m.p. 145.5°–148° C. (acetonitrile).

68. (E)-(RS)-3-[5-(2,4-Diamino-pyrimidin-5-ylmethyl)-2,3-dimethoxy-phenyl]-1-[1-[5-(2-hydroxy-ethyl)-2-methyl-2H-pyrazol-3-yl]-3,4-dihydro-1H-isoquinolin-2-yl]-propenone, beige foam, MS (ISP): 570.3 (M+H)⁺.

69. Methyl (E)-(RS)-[5-[2-[3-[5-(2,4-diamino-pyrimidin-5-ylmethyl)-2,3-dimethoxy-phenyl]-acryloyl]-1,2,3,4-tetrahydro-isoquinolin-1-yl]-1-methyl-1H-pyrazol-3-yl]-acetate, m.p. 204°–206° C. dec. (acetonitrile).

70. (E)-(RS)-3-[5-(2,4-Diamino-pyrimidin-5-ylmethyl)-2,3-dimethoxy-phenyl]-1-[1-(5-hydroxymethyl-2-methyl-2H-pyrazol-3-yl)-3,4-dihydro-1H-isoquinolin-2-yl]-propenone, beige foam, MS (ISP): 556.5 (M+H)⁺.

EXAMPLE 71

A solution of 1.33 g of 5-(3-iodo-4,5-dimethoxy-benzyl)-pyrimidine-2,4-diamine, 1.16 g of (RS)-1-[1-(2,5-dimethyl-2H-pyrazol-3-yl)-3,4-dihydro-1H-isoquinolin-2-yl]-propenone and 0.44 g of triethylamine in 5.2 ml of N,N-dimethylformamide was treated with 0.121 g of bis(triphenyl-phosphine)-palladium(II) dichloride and heated to 120° C. for 30 min. Subsequently, the mixture was poured into 120 ml of cold sodium hydrogen carbonate solution and stirred at room temperature for 10 min. The resulting precipitate was filtered off under suction, dried and purified over silica gel with dichloromethane/methanol 95:5. There was obtained 0.89 g (48%) of (E)-(RS)-3-[5-(2,4-diamino-pyrimidin-5-ylmethyl)-2,3-dimethoxy-phenyl]-1-[1-(2,5-dimethyl-2H-pyrazol-3-yl)-3,4-dihydro-1H-isoquinolin-2-yl]-propenone as a colorless solid with decomposition at >130° C. MS (ISP): 540.3 (M+H)⁺.

The following compounds were prepared in analogy to the preparation of (E)-(RS)-3-[5-(2,4-diamino-pyrimidin-5-ylmethyl)-2,3-dimethoxy-phenyl]-1-[1-(2,5-dimethyl-2H-pyrazol-3-yl)-3,4-dihydro-1H-isoquinolin-2-yl]-propenone described above:

EXAMPLES 72–80

72. (E)-(RS)-3-[5-(2,4-Diamino-pyrimidin-5-ylmethyl)-2,3-dimethoxy-phenyl]-1-[1-(4-methyl-[1,2,3]thiadiazol-5-yl)-3,4-dihydro-1H-isoquinolin-2-yl]-propenone, MS (ISP): 544 (M+H)$^+$.

73. (E)-(RS)-3-[5-(2,4-Diamino-pyrimidin-5-ylmethyl)-2,3-dimethoxy-phenyl]-1-[1-(1H-[1,2,4]triazol-3-yl)-3,4-dihydro-1H-isoquinolin-2-yl]-propenone, MS (ISP): 513.5 (M+H)$^+$.

74. (E)-(RS)-3-[5-(2,4-Diamino-pyrimidin-5-ylmethyl)-2,3-dimethoxy-phenyl]-1-[1-(5-methyl-1H-imidazol-4-yl)-3,4-dihydro-1H-isoquinolin-2-yl]-propenone, m.p. 170° C. dec. (acetonitrile).

75. (E)-(RS)-3-[5-(2,4-Diamino-pyrimidin-5-ylmethyl)-2,3-dimethoxy-phenyl]-1-[1-(5-pyridin-2-yl-thiophen-2-yl)-3,4-dihydro-1H-isoquinolin-2-yl]-propenone, m.p. 162°–164° C. (dichloromethane).

76. (E)-(RS)-3-[5-(2,4-Diamino-pyrimidin-5-ylmethyl)-2,3-dimethoxy-phenyl]-1-[1-(5-furan-2-yl-thiazol-4-yl)-3,4-dihydro-1H-isoquinolin-2-yl]-propenone, m.p. >140° C., dec. (acetonitrile).

77. (E)-(RS)-1-[1-(1-Benzyl-5-methyl-1H-pyrazol-3-yl)-3,4-dihydro-1H-isoquinolin-2-yl]-3-[5-(2,4-diamino-pyrimidin-5-ylmethyl)-2,3-dimethoxy-phenyl]-propenone, m.p. 207°–208° C. (ethanol).

78. (E)-(RS)-3[-5-(2,4-Diamino-pyrimidin-5-ylmethyl)-2,3-dimethoxy-phenyl]-1-[1-(5-methyl-2H-pyrazol-3-yl)-3,4-dihydro-1H-isoquinolin-2-yl]-propenone, m.p. 232°–233° C.

79. (E)-(RS)-3-[5-(2,4-Diamino-pyrimidin-5-ylmethyl)-2,3-dimethoxy-phenyl]-1-[1-(2-pyridin-3-yl-thiazol-4-yl)-3,4-dihydro-1H-isoquinolin-2-yl]-propenone, m.p. >130° C., dec. (ethanol).

80. (E)-(RS)-3-[5-(2,4-Diamino-pyrimidin-5-ylmethyl)-2,3-dimethoxy-phenyl]-1-[1-(3-dimethylamino-1-methyl-1H-pyrazol-4-yl)- 3,4-dihydro-1H-isoquinolin-2-yl]-propenone, m.p. 185°–188° C. (acetonitrile).

EXAMPLE 81

273 mg of (E)-(RS)-4-[2-[3-[5-(2,4-diamino-pyrimidin-5-yl)-2,3-dimethoxy-phenyl]-acryloyl]-1,2,3,4-tetrahydro-isoquinolin-1-yl]-benzonitrile in 3 ml of N,N-dimethylformamide were treated with 36 mg of sodium azide and 29 mg of ammonium chloride and stirred at 90° C. for 30 h. Thereafter, the reaction mixture was evaporated to dryness and the residue was subjected to chromatography on MCI (25 cm×2.5 cm Ø) with the eluent water/ethanol (0–100%, v/v). The pure fractions were combined and concentrated. Recrystallization of the colorless residue from ethanol/hexane yielded 74 mg of (E)-(RS)-3-[5-(2,4-diamino-pyrimidin-5-ylmethyl)-2,3-dimethoxy-phenyl]-1-[1-[4-(2H-tetrazol-5-yl)-phenyl]-3,4-dihydro-1H-isoquinolin-2-yl]-propenone, m.p. 208°–215° C.

EXAMPLE 82

In analogy to Example 81, from (E)-(RS)-2-[3-[5-(2,4-diamino-pyrimidin-5-ylmethyl)-2,3-dimethoxy-phenyl]-acryloyl]-1,2,3,4-tetrahydro-isoquinoline-1-carbonitrile Example 28) there was obtained (E)-(RS)-3-[5-(2,4-diamino-pyrimidin-5-ylmethyl)-2,3-dimethoxy-phenyl]-1-[1-(2H-tetrazol-5-yl)-3,4-dihydro-1H-isoquinolin-2-yl]-propenone as a beige solid, m.p. 179° C., dec. (ethanol).

The starting materials (compounds of formula II) used in Example 1–82, the preparation of which has hitherto not been described, can be prepared as described hereinafter or in analogy thereto.

A. Carboxylic acid phenethylamine derivatives a) A mixture of 20 ml of ethyl pyridine-2-carboxylate and 27 ml of phenethylamine was stirred at 180° C. for 5 h., with the ethanol formed being distilled off over a 30 cm Vigreux column. Distillation of the residue yielded 30.9 g of pyridine-2-carboxylic acid phenethyl-amide as a yellowish oil, b.p. 150°–155° C./0.8 mbar.

The following compounds were obtained in analogy to the preparation of pyridine-2-carboxylic acid phenethylamide described under Aa):

4-Methoxy-N-phenethyl-benzamide, m.p. 58°–59° C. (diisopropyl ether), (Example 8);

pyrazine-2-carboxylic acid phenethyl-amide, m.p. 95°–97° C. (diisopropyl ether), (Example 10);

pyridine-2-carboxylic acid [2-(4-chloro-phenyl)-ethyl]-amide, m.p. 85°–86° C. (diisopropyl ether), (Example 11);

pyridine-2-carboxylic acid [2-(4-methyl-phenyl)-ethyl]-amide, b.p. 165° C./0.12 mbar, (Example 12);

4-chloro-pyridine-2-carboxylic acid phenethyl-amide, m.p. 65° C. (diisopropyl ether), (Example 33);

4-diethylaminomethyl-N-phenethyl-benzamide, m.p. 87°–88° C. (diisopropyl ether), (Example 38);

pyridine-2,5-dicarboxylic acid 2-amide 5-(phenethyl-amide), m.p. 240° C. (ethanol), (Example 39);

5-m8ethyl-1H-imidazole-4-carboxylic acid phenethyl-amide, m.p. 132° C. (ethyl acetate), (Example 74).

b) A solution of 10 g of 6-chloro-nicotinic acid in 80 ml of N,N-dimethylformamide and 160 ml of tetrahydrofuran was treated with 10.75 g of 1,1'-carbonyldiimidazole and stirred at room temperature for 4 h. Thereafter, the reaction mixture was treated with 8.76 g of phenethylamine and stirred at 70° C. for a further 2 h. The mixture was cooled to room temperature, evaporated to dryness and the residue was taken up in 200 ml of dichloromethane. The organic phase was washed three times with 50 ml of water each time, dried over sodium sulfate and evaporated to dryness. Recrystallization of the residue from isopropanol yielded 11.9 g of 6-chloro-pyridine-3-carboxylic acid phenethyl-amide as a colorless product, m.p. 115° C.

The following compounds were obtained in analogy to the preparation of 6-chloro-pyridine-3-carboxylic acid phenethyl-amide described under Ab):

Pyrimidine-5-carboxylic acid phenethyl-amide, m.p. 95°–96° C. (ethyl acetate/hexane), (Example 15);

pyrimidine-4-carboxylic acid phenethyl-amide, m.p. 80°–81° C. (ethyl acetate/hexane), (Example 17);

pyridazine-3-carboxylic acid phenethyl-amide, m.p. 82°–83° C. (ethyl acetate/hexane), (Example 25);

3,6-dichloro-pyridazine-4-carboxylic acid phenethyl-amide, m.p. 103°–105° C. (ethyl acetate/hexane), (Example 26);

6-hydroxy-N-phenethyl-nicotinamide, m.p. 216° C. (ethanol), (Example 30);

6-methyl-pyridine-3-carboxylic acid phenethyl-amide, m.p. 107° C. (diisopropyl ether), (Example 32);

5-chloro-pyridine-2-carboxylic acid phenethyl-amide, m.p. 74°–76° C. (hexane), (Example 34);

6-dimethylamino-N-phenethyl-nicotinamide, m.p. 126°–127° C. (isopropanol/diisopropyl ether), (Example 35);

4-methoxy-1-oxy-pyridine-2-carboxylic acid phenethyl-amide, (Example 41);

pyridine-2,5-dicarboxylic acid 2-amide γ-(phenethyl-amide), m.p. 240° C. (ethanol), (Example 42);

4-bromo-pyridine-2-carboxylic acid phenethyl-amide, m.p. 58°–60° C., (Example 44);

4-morpholin-4-ylmethyl-N-phenethyl-benzamide, m.p. 120°–121° C. (ethyl acetate/hexane), (Example 48);

4-(4-methyl-piperazin-1-ylmethyl)-N-phenethyl-benzamide, m.p. 131°–133° C. (ethyl acetate/hexane), (Example 50);

4-imidazol-1-ylmethyl-N-phenethyl-benzamide, m.p. 162°–163° C. (isopropanol), (Example 52);

N-phenethyl-4-[1,2,4]triazol-1-ylmethyl-benzamide, m.p. 142.5°–143.5° C. (isopropanol/diisopropyl ether), (Example 54);

4-methylsulphanyl-N-phenethyl-benzamide, m.p. 136° C. (ethyl acetate), (Example 55);

3-methanesulphonyl-N-phenethyl-benzamide, m.p. 112° C. (ethyl acetate), (Example 56);

6-methylsulphanyl-N-phenethyl-nicotinamide, m.p. 135° C. (ethyl acetate), (Example 57);

5-pyridin-2-yl-thiophene-2-carboxylic acid phenethyl-amide, m.p. 131°–133° C. (ethyl acetate), (Example 75);

1-benzyl-5-methyl-1H-pyrazole-3-carboxylic acid phenethyl-amide, m.p. 87°–87.5° C. (ethyl acetate), (Example 77);

5-methyl-2H-pyrazole-3-carboxylic acid phenethyl-amide, m.p. 117°–117.5° C. (ethyl acetate), (Example 78);

2-pyridin-3-yl-thiazole-4-carboxylic acid phenethyl-amide, m.p. 102°–103° C., (Example 79);

3-dimethylamino-1-methyl-1H-pyrazole-4-carboxylic acid phenethyl-amide, m.p. 98°–98.5° C., (Example 80).

c) A solution of 1.68 g of ethyl 2,5-dimethyl-2H-pyrazole-3-carboxylate in 3.8 ml of phenethylamine was treated with 0.10 g of rhodium(III) trichloride.trihydrate and heated to 140° C. while stirring for 21 h. Subsequently, the mixture was taken up in ethyl acetate/water, adjusted to pH 2–3 with 2N HCl and extracted three times with ethyl acetate. The combined organic phases were washed neutral with sat. aqueous sodium chloride solution, dried over sodium sulfate and evaporated. Chromatographic purification on silica gel with hexane/ethyl acetate 50:50 yielded 1.92 g (79%) of cryst. product of m.p. 97°–98° C. Recrystallization of a sample from tBuOMe gave 2,5-dimethyl-2H-pyrazole-3-carboxylic acid phenethyl-amide as colorless crystals of m.p. 97.5°–98.5° C.

The following compounds were obtained in analogy to the preparation of 2,5-dimethyl-2H-pyrazole-3-carboxylic acid phenethyl-amide described under Ac):

2-Methyl-4-morpholin-4-ylmethyl-2H-pyrazole-3-carboxylic acid phenylamide, m.p. 90.5°–91.5° C., (Example 62);

1-methyl-5-(4-methyl-piperazin-1-ylmethyl)-1H-pyrazole-3-carboxylic acid phenethylamide, m.p. 115°–116° C., (Example 63);

1-methyl-4-morpholin-4-ylmethyl-1H-pyrazole-3-carboxylic acid phenethylamide, m.p. 106°–108° C., (Example 64);

2-methyl-5-morpholin-4-ylmethyl-2H-pyrazole-3-carboxylic acid phenethylamide, m.p. 113°–114° C., (Example 65);

1H-[1,2,4]triazole-3-carboxylic acid phenethylamide, m.p. 199°–200° C. (water), (Example 73);

5-furan-2-yl-thiazole-4-carboxylic acid phenethylamide, m.p. 53.5°–55.5° C. and b.p. 190°–195° C./0.1 mbar (bulb-tube), (Example 76).

d) A suspension of 9.65 g of 4-methyl-[1,2,3]thiadiazol-5-carboxylic acid in 70 ml of dichlormethane was cooled to 5° C. while stirring, treated with 0.15 g of 4-dimethylamino-pyridine and subsequently with 13.8 g of N,N'-dicyclohexyl-carbodiimide at such a rate that the internal temperature <10° C. could be maintained. After completion of the addition, the mixture was cooled to 5° C. and 8.92 g of phenethylamine were added at such a rate that the internal temperature of <37° C. could be maintained. After completion of the addition, the mixture was stirred for a further 1 h., then the precipitate was filtered off under suction, rinsed well with dichloromethane and the filtrate was evaporated. The residual yellow oil was subjected to chromatography on silica gel with hexane/ethyl acetate 50:50. There were obtained 15.66 g (92%) of 4-methyl-[1,2,3]thiadiazole-5-carboxylic acid phenethylamide as a colorless crystallizate of m.p. 64°–68° C. Recrystallization of a sample from tert.-butyl methyl ether gave colorless crystals of m.p. 64.5°–66° C.

e) 4-Methoxy-pyridine-2-carboxylic acid phenethyl-amide. b.p. 160° C./0.08 mbar (bulb-tube), was prepared by reacting 4-methoxy-1-oxy-pyridine-2-carboxylic acid phenethylamide with phosphorus trichloride in chloroform. (Example 41).

f) 6-Morpholin-4-yl-N-phenethyl-nicotinamide, m.p. 163°–165° C. (ethanol), was obtained by reacting 6-chloro-pyridine-3-carboxylic acid phenethylamide with morpholine in boiling isopropanol for 8 days. (Example 45).

6-(4-Methyl-piperazin-1-yl)-N-phenethyl-nicotinamide hydrochloride, m.p. >280° C. (acetonitrile), was obtained by reacting 6-chloro-pyridine-3-carboxylic acid phenethylamide with 1-methylpiperazine in boiling isopropanol for 7 days. (Example 47).

4-Imidazol-1-yl-N-phenethyl-benzamide, m.p. 160° C. (ethyl acetate), was prepared by reacting 4-fluoro-N-phenethyl-benzamide with imidazole in dimethyl sulfoxide in the presence of potassium carbonate for 5 days at 100° C. (Example 51).

N-Phenethyl-4-[1,2,4]triazol-1-yl-benzamide, m.p. 175°–176° C. (ethyl acetate), was prepared by reacting 4-fluoro-N-phenethyl-benzamide with 1H-[1,2,4]triazole in dimethyl sulfoxide in the presence of potassium carbonate for 3 days at 100° C. (Example 53).

g) 4-Dimethylamino-pyridine-2-carboxylic acid phenethyl-amide, m.p. 110°–112° C. (diisopropyl ether), was obtained by reacting 4-bromo-pyridine-2-carboxylic acid phenethylamide with dimethylamine in ethanol for 18 h. at 160° C. (Example 44).

h) 2-Methyl-5-cyanomethyl-2H-pyrazole-3-carboxylic acid phenethyl-amide, m.p. 117°–118° C., was prepared by reacting 5-bromomethyl-2-methyl-2H-pyrazole-3-carboxylic acid phenethylamide (Example 66) with sodium cyanide in dimethyl sulfoxide (DMSO) at 90° C. for 20 minutes. (Example 66).

i) 1-Methyl-5-morpholin-4-ylmethyl-1H-pyrazole-3-carboxylic acid phenethylamide, m.p. 133°–134° C., was prepared by reacting 5-bromomethyl-1-methyl-1H-pyrazole-3-carboxylic acid phenethylamide (E. Example 67) with morpholine in acetone at room temperature for 2.5 hours. (Example 67).

i) Ethyl 1-methyl-5-phenethylcarbamoyl-1H-pyrazole-3-carboxylate, m.p. 99°–101° C., was prepared by reacting 1-methyl-1H-pyrazole-3,5-dicarboxylic acid 3-ethyl ester (E. Example 70) with N,N'-carbonyldiimidazole in dichloromethane at room temperature for 2 hours, then adding phenethylamine and stirring at room temperature for a further 2 hours. (Example 70).

B. 3.4-Dihydro-isoquinoline derivatives a) A mixture of 14 g of pyridine-2-carboxylic acid phenethyl-amide and 300 g of polyphosphoric acid was stirred at 140° C. for 90 min., at 150° C. for 60 min. and finally at 155° C. for 60 min. The solution was cooled to 120° C. and poured into 2 l of water while stirring. The mixture was stirred at room temperature for a further 15 min. and made basic (strong warming!) by the addition of about 300 ml of 25% ammonium hydroxide while cooling with ice and stirring. Thereafter, the mixture was extracted with 2×400 ml of ethyl acetate. The combined raspberry-red organic phases were washed with 100 ml of 10% sodium chloride solution, dried over sodium sulfate, treated with about 5 g of Darco G60 and evaporated to dryness. There were obtained 11.6 g of 1-pyridin-2-yl-3,4-dihydro-isoquinoline as a yellowish oil, b.p. 130° C./0.08 mbar (bulb-tube).

The following compounds were obtained in analogy to the preparation of 1-pyridin-2-yl-3,4-dihydro-isoquinoline described under Ba):

7-Methoxy-1-pyridin-2-yl-3,4-dihydro-isoquinoline, b.p. 180° C./0.07 mbar, (Example 8);
1-pyrazin-2-yl-3,4-dihydro-isoquinoline, b.p. about 135° C./0.09 mbar, (Example 10);
7-chloro-1-pyridin-2-yl-3,4-dihydro-isoquinoline, b.p. about 165° C./0.06 mbar, (Example 11);
7-methyl-1-pyridin-2-yl-3,4-dihydro-isoquinoline, b.p. 165° C./0.12 mbar, (Example 12);
1-pyrimidin-5-yl-3,4-dihydro-isoquinoline, m.p. 61°–63° C. (ethyl acetate/hexane), (Example 15);
1-pyrimidin-4-yl-3,4-dihydro-isoquinoline, MS (EI): 209M$^+$. (Example 17);
1-pyridazin-3-yl-3,4-dihydro-isoquinoline, m.p. 96°–98° C., dec. (methylene chloride/hexane), (Example 25);
1-(3,6-dichloro-pyridazin-4-yl)-3,4-dihydro-isoquinoline, m.p. 120°–122° C. (ethyl acetate/hexane), (Example 26);
5-(3,4-dihydro-isoquinolin-1-yl)-1H-pyridin-2-one, m.p. 155°–156° C. (acetonitrile), (Example 30);
1-(6-methyl-pyridin-3-yl)-3,4-dihydro-isoquinoline, m.p. 68° C., (Example 32);
1-(4-chloro-pyridin-2-yl)-3,4-dihydro-isoquinoline, b.p. about 145° C./0.1 mbar, (Example 33);
1-(5-chloro-pyridin-2-yl)-3,4-dihydro-isoquinoline, m.p. 53°–54° C., (Example 34);
[5-(3,4-dihydro-isoquinolin-1-yl)-pyridin-2-yl]-dimethyl-amine, b.p. 160° C./0.055 mbar, (Example 35);
1-(6-chloro-pyridin-3-yl)-3,4-dihydro-isoquinoline, m.p. 68° C. (hexane), (Example 36);
[4-(3,4-dihydro-isoquinolin-1-yl)-benzyl]-diethyl-amine, b.p. 180° C./0.2 mbar, (Example 38);
5-(3,4-dihydro-isoquinolin-1-yl)-pyridine-2-carboxamide, m.p. 167° C. (ethanol) (Example 39);
1-(4-methoxy-pyridin-2-yl)-3,4-dihydro-isoquinoline, b.p. 140° C./0.08 mbar (bulb-tube), (Example 41);
5-(3,4-dihydro-isoquinolin-1-yl)-pyridin-2-carboxamide, m.p. 167° C. (ethanol), (Example 42);
[2-(3,4-dihydro-isoquinolin-1-yl)-pyridin-4-yl]-dimethyl-amine, m.p. 124°–126° C. (diisopropyl ether), (Example 44);
1-(6-morpholin-4-yl-pyridin-3-yl)-3,4-dihydro-isoquinoline, m.p. 88°–89° C., (Example 45);
1-[6-(4-methyl-piperazin-1-yl)-pyridin-3-yl]-3,4-dihydro-isoquinoline, m.p. 103°–104° C. (diisopropyl ether), (Example 47);
1-(4-morpholin-4-ylmethyl-phenyl)-3,4-dihydro-isoquinoline, m.p. 122°–124° C. (hexane), (Example 48);
4-(3,4-dihydro-isoquinolin-1-yl)-benzamide, m.p. 205° C. (ethyl acetate), (Example 49);
1-[4-(4-methyl-piperazin-1-ylmethyl)-phenyl]-3,4-dihydro-isoquinoline, b.p. 185° C./0.1 mbar (bulb-tube), (Example 50);
1-(4-imidazol-1-yl-phenyl)-3,4-dihydro-isoquinoline, m.p. 121° C. (ethyl acetate), (Example 51);
1-(4-imidazol-1-ylmethyl-phenyl)-3,4-dihydro-isoquinoline, m.p. 151°–152° C. (isopropanol/diisopropyl ether), (Example 52);
1-(4-[1,2,4]triazol-1-yl-phenyl)-3,4-dihydro-isoquinoline, m.p. 161° C. (ethanol), (Example 53);
1-(4-[1,2,4]triazol-1-ylmethyl-phenyl)-3,4-dihydro-isoquinoline, m.p. 108° C. (isopropanol/diisopropyl ether), (Example 54);
1-(4-methylsulphanyl-phenyl)-3,4-dihydro-isoquinoline, m.p. 83° C. (diisopropyl ether), (Example 55);
1-(3-methanesulphonyl-phenyl)-3,4-dihydro-isoquinoline, m.p. 130° C. (ethyl acetate), (Example 56);
1-(6-methylsulphanyl-pyridin-3-yl)-3,4-dihydro-isoquinoline, m.p. 95° C. (diisopropyl ether), (Example 57);
1-(2-methyl-4-morpholin-4-ylmethyl-2H-pyrazol-3-yl)-3,4-dihydro-isoquinoline, yellow oil, MS (TSP): 310M$^+$, (Example 62);
1-[1-methyl-5-(4-methyl-piperazin-1-ylmethyl)-1H-pyrazol-3-yl]-3,4-dihydro-isoquinoline, m.p. 79.5°–82° C., (Example 63);
1-(1-methyl-4-morpholin-4-ylmethyl-1H-pyrazol-3-yl)-3,4-dihydro-isoquinoline, brown oil, MS (ISP): 311.2 (M+H)$^+$, (Example 64);
1-(2-methyl-5-morpholin-4-ylmethyl-2H-pyrazol-3-yl)-3,4-dihydro-isoquinoline, brown oil, MS (EI): 310M$^{30}$, (Example 65);
2-[γ-(3,4-dihydro-isoquinoline-1-yl)-1-methyl-1H-pyrazol-3-yl]-acetamide, m.p. 182°–185° C., (Examples 66 and 68);
1-(1-methyl-5-morpholin-4-ylmethyl-1H-pyrazol-3-yl)-3,4-dihydro-isoquinoline, yellow oil, MS (ISP): 311.3 (M+H)$^+$, (Example 67);
5-(3,4-dihydro-isoquinolin-1-yl)-1-methyl-1H-pyrazole-3-carboxylic acid, yellow foam, MS (ISP): 256.3 (M+H)$^+$, (Example 70);
1-(1H-[1,2,4]triazol-3-yl)-3,4-dihydro-isoquinoline, m.p. 165°–166° C. (ethyl acetate), (Example 73);
1-(5-methyl-1H-imidazol-4-yl)-3,4-dihydro-isoquinoline, m.p. 214°–216° C., (Example 74);
1-(5-pyridin-2-yl-thiophen-2-yl)-3,4-dihydro-isoquinoline, m.p. 141°–143° C. (ethyl acetate), (Example 75);
1-(5-furan-2-yl-thiazol-4-yl)-3,4-dihydro-isoquinoline, m.p. 101°–104° C., (Example 76);
1-(5 -methyl-2H-pyrazol-3 -yl)-3,4-dihydro-isoquinoline, beige foam, MS (ISP): 212.2 (M+H)$^+$, (Example 78);
1-(3-dimethylamino-1-methyl-1H-pyrazol-4-yl)-3,4-dihydro-isoquinoline, m.p. 102°–103° C., (Example 80).

b) A solution of 10.54 g of 2,5-dimethyl-2H-pyrazole-3-carboxylic acid phenethylamide in 90 ml of toluene was treated with 11.1 g of phosphorus pentachloride and the suspension was heated to reflux for 1 h. Subsequently, it was cooled to about 50° C., treated with 11.1 g of anhydrous aluminium trichloride in one portion and heated to reflux for a further 3 h. After cooling to room temperature, 90 ml of deionised water were added dropwise while cooling with ice. After stirring vigorously for 5 min., the organic phase was separated, washed twice with water and the combined aqueous phases were again washed twice with diethyl ether. The aqueous phase was adjusted to pH >12 with 28% sodium hydroxide solution and extracted with ethyl acetate. Washing of the combined organic phases with sat. aqueous sodium chloride solution, drying over sodium sulfate and evaporation gave 9.01 g (92%) of a brown oil. Bulb-tube distillation of a sample gave 1-(2,5-dimethyl-2H-pyrazol-3-yl)-3,4-dihydro-isoquinoline as a colorless oil of b.p. 120°–125° C./0.2 mbar.

The following compounds were obtained in analogy to the preparation of 1-(2,5-dimethyl-2H-pyrazol-3-yl)-3,4-dihydro-isoquinoline described under Bb):

1-(4-Methyl-[1,2,3]thiadiazol-5-yl)-3,4-dihydro-isoquinoline, m.p. 111.5°–112° C. (ethyl acetate), (Example 72);

1-(1-benzyl-5-methyl-1H-pyrazol-4-yl)-3,4-dihydro-isoquinoline, m.p. 84°–84.5° C., (Example 77);

1-(2-pyridin-3-yl-thiazol-4-yl)-3,4-dihydro-isoquinoline, b.p. 220°–230° C./0.3 mbar (bulb-tube), (Example 79).

c) 2-{[5-(3,4-Dihydro-isoquinolin-1-yl)-pyridin-2-yl]-methyl-amino}-ethanol, m.p. 115° C. (ethyl acetate/diisopropyl ether), was prepared by reacting 1-(6-chloro-pyridin-3-yl)-3,4-dihydro-isoquinoline with 2-methylamino-ethanol in boiling ethanol for 3 days. (Example 58).

d) Methyl [5-(3,4-dihydro-isoquinolin-1-yl)-1-methyl-1H-pyrazol-3-yl]-acetate, brown oil, MS (ISP): 284.2 (M+H)$^+$, was prepared by reacting 2-[5-(3,4-dihydro-isoquinolin-1-yl)-1-methyl-1H-pyrazol-3-yl]-acetamide (B. Examples 66 and 68) with N,N-dimethylformamide dimethyl acetal at room temperature for 18 h. (Examples 68 and 69).

C. 1,2,3,4-Tetrahydro-isoquinoline derivatives (compounds of formula IV)

a) A solution of 6.1 g of 1-pyridin-2-yl-3,4-dihydro-isoquinoline in 220 ml of absolute ethanol was hydrogenated on 1.25 g of platinum dioxide at 20° C. and 1 bar hydrogen pressure for 90 min. After removal of the catalyst by filtration, [the filtrate] was concentrated under reduced pressure. There were obtained 6.71 g of (RS)-1-pyridin-2-yl-1,2,3,4-tetrahydro-isoquinoline as a colorless oil, b.p. 140° C./0.1 mbar (bulb-tube).

A solution of 22.2 g of (RS)-1-pyridin-2-yl-1,2,3,4-tetrahydro-isoquinoline in 500 ml of warm absolute ethanol was treated with 15.85 g of D-(−)-tartaric acid. After filtration of the slightly turbid solution, the clear solution obtained was left to stand at 20° C. for 6 h. and at 5° C. for a further 18 h. The precipitate formed was filtered off under suction and washed with absolute ethanol. A second crystallizate was obtained immediately from the mother liquor. The precipitates were combined (15.0 g, m.p. 155°–158° C.) and recrystallized from 900 ml of absolute ethanol. There were obtained 11.4 g of (R)-1-pyridin-2-yl-1,2,3,4-tetrahydro-isoquinoline (2S,3S)-2,3-dihydroxy-succinate (1:1) as a colorless product, m.p. 162°–165° C.

A solution of 11.16 g of (R)-1-pyridin-2-yl-1,2,3,4-tetrahydro-isoquinoline (2S,3S)-2,3-dihydroxy-succinate (1:1) was dissolved in 100 ml of water and treated with 10 ml of a 25% aqueous ammonia solution. The mixture was extracted with 2×100 ml of diethyl ether. The combined organic phases were washed with 100 ml of water, dried over sodium sulfate and evaporated to dryness. The residue was distilled in a bulb-tube in order to give 6.35 g of (R)-1-pyridin-2-yl-1,2,3,4-tetrahydro-isoquinoline as a colorless oil, b.p. 135° C./0.15 mbar, which crystallized upon standing, m.p. 50°–52° C.

The following compounds were obtained in analogy to the preparation of (RS)-1-pyridin-2-yl-1,2,3,4-tetrahydro-isoquinoline described under Ca):

(RS)-1-Pyridin-4-yl-1,2,3,4-tetrahydro-isoquinoline, m.p. 124° C. (ethyl acetate), (Example 6);

(RS)-7-methoxy-1-pyridin-2-yl-3,4-dihydro-isoquinoline, b.p. 157° C./0.07 mbar, (Example 8);

(RS)-1-pyrazin-2-yl-1,2,3,4-tetrahydro-isoquinoline, m.p. 75°–76° C. (hexane), (Example 10);

(R,S)-7-chloro-1-pyridin-2-yl-1,2,3,4-tetrahydro-isoquinoline, b.p. 175° C./0.4 mbar, (Example 11);

(RS)-7-methyl-1-pyridin-2-yl-1,2,3,4-tetrahydro-isoquinoline, b.p. 150° C./0.1 mbar, (Example 12);

(RS)-1-pyrimidin-5-yl-1,2,3,4-tetrahydro-isoquinoline, m.p. 75°–77° C. (methylene chloride/cyclohexane), (Example 15);

(RS)-1-pyrimidin-4-yl-1,2,3,4-tetrahydro-isoquinoline hydrochloride (1:1.7), m.p. 150° C., dec. (ethanol), (Example 17);

(RS)-1-pyridazin-3-yl-1,2,3,4-tetrahydro-isoquinoline, m.p. 76°–78° C. (dichloromethane/hexane), (Example 25);

(RS)-1-pyridazin-4-yl-1,2,3,4-tetrahydro-isoquinoline hydrochloride (1:1.7), m.p. 115° C., dec. (ethanol), (Example 26);

(RS)-1-(6-methyl-pyridin-3-yl)-1,2,3,4-tetrahydro-isoquinoline, m.p. 82° C. (hexane), (Example 32);

(RS)-dimethyl-[5-(1,2,3,4-tetrahydro-isoquinolin-1-yl)-pyridin-2-yl]-amine, m.p. 94°–95° C. (diisopropyl ether), (Example 35);

(RS)-diethyl-[4-(1,2,3,4-tetrahydro-isoquinolin-1-yl)-benzyl]-amine, b.p. 160° C./0.055 mbar, (Example 38);

(R,S)-5-(1,2,3,4-tetrahydro-isoquinolin-1-yl)-pyridine-2-carboxamide, m.p. 200° C. (isopropanol), (Example 39);

(R,S)-1-(4-methanesulphonyl-phenyl)-1,2,3,4-tetrahydro-isoquinoline, m.p. 118°–120° C. (diisopropyl ether), (Example 40);

(RS)-1-(4-methoxy-pyridin-2-yl)-1,2,3,4-tetrahydro-isoquinoline, b.p. 130° C./0.05 mbar, (Example 41);

(RS)-5-(1,2,3,4-tetrahydro-isoquinolin-1-yl)-pyridine-2-carboxamide, m.p. 200° C. (isopropanol), (Example 42);

(RS)-dimethyl-[2-(1,2,3,4-tetrahydro-isoquinolin-1-yl)-pyridin-4-yl]-amine, m.p. 106°–109° C. (diisopropyl ether), (Example 44);

(RS)-1-(6-morpholin-4-yl-pyridin-3-yl)-1,2,3,4-tetrahydro-isoquinoline, m.p. 151°–152° C. (isopropanol), (Example 45);

(RS)-1-[6-(4-methyl-piperazin-1-yl)-pyridin-3-yl]-1,2,3,4-tetrahydro-isoquinoline, m.p. 132.5°–133.5° C. (diisopropyl ether), (Example 47);

(RS)-1-(4-morpholin-4-ylmethyl-phenyl)-1,2,3,4-tetrahydro-isoquinoline, m.p. 128°–129° C. (hexane), (Example 48);

(RS)-4-(1,2,3,4-tetrahydro-isoquinolin-1-yl)-benzamide, m.p. 208° C. (ethanol), (Example 49);

(RS)-1-[4-(4-methyl-piperazin-1-ylmethyl)-phenyl]-1,2,3,4-tetrahydro-isoquinoline, m.p. 96°–98° C. (hexane), (Example 50°);

(RS)-1-(4-imidazol-1-yl-phenyl)-1,2,3,4-tetrahydro-isoquinoline, m.p. 125° C. (ethyl acetate), (Example 51);

(RS)-1-(4-imidazol-1-ylmethyl-phenyl)-1,2,3,4-tetrahydro-isoquinoline, m.p. 133° C. (ethyl acetate/diisopropyl ether), (Example 53);

(RS)-1-(1-methyl-4-morpholin-4-ylmethyl-1H-pyrazol-3-yl)-1,2,3,4-tetrahydro-isoquinoline, yellowish oil, MS (ISP): 313.2 (M+H)$^+$, (Example 64);

(RS)-1-(2-methyl-5-morpholin-4-ylmethyl-2H-pyrazol-3-yl)-1,2,3,4-tetrahydro-isoquinoline, yellowish oil, MS (ISP): 313.2 (M+H)$^+$, (Example 65);

(RS)-2-[1-methyl-5-(1,2,3,4-tetrahydro-isoquinolin-1-yl)-1H-pyrazol-3-yl]-acetamide, m.p. 145°–146° C., (ethyl acetate/diethyl ether), (Example 66);

(RS)-1-(1-methyl-5-morpholin-4-ylmethyl-1H-pyrazol-3-yl)-1,2,3,4-tetrahydro-isoquinoline, yellowish oil, MS (ISP): 313.3 (M+H)$^+$, (Example 67);

methyl (RS)-[1-methyl-5-(1,2,3,4-tetrahydro-isoquinolin-1-yl)-1H-pyrazol-3-yl]-acetate, yellow oil, MS (EI): 285M$^{30}$, (Example 69).

b) A solution of 3.48 g of 4-(3,4-dihydro-isoquinolin-1-yl)-benzonitrile in 90 ml of methanol was cooled to 5° C. while stirring and treated with 1.7 g of sodium borohydride within 30 min. After completion of the addition, the mixture was stirred at 5° C. for a further 30 min. Subsequently, 50 ml of water were slowly added dropwise and the mixture was stirred at room temperature for a further 10 min. The mixture was diluted with water and extracted three times with ethyl acetate. The combined organic phases were dried over sodium sulfate and evaporated. 3.15 g of crystalline (RS)-4-(1,2,3,4-tetrahydro-isoquinolin-1-yl)-benzonitrile were obtained. Recrystallization of a sample from diisopropyl ether gave colorless crystals of m.p. 94°–97° C.

The following compounds were obtained in analogy to the preparation of (RS)-4-(1,2,3,4-tetrahydro-isoquinolin-1-yl)-benzonitrile described under Cb):

(RS)-5-(1,2,3,4-Tetrahydro-isoquinolin-1-yl)-1H-pyridin-2-one, m.p. 114°–115° C. (acetonitrile), (Example 30);

(RS)-1-(4-chloro-pyridin-2-yl)-1,2,3,4-tetrahydro-isoquinoline, b.p. about 140° C./0.1 mbar, (Example 33);

(RS)-1-(5-chloro-pyridin-2-yl)-1,2,3,4-tetrahydro-isoquinoline, m.p. 92°–93° C. (hexane), (Example 34);

(RS)-1-(6-chloro-pyridin-3-yl)-1,2,3,4-tetrahydro-isoquinoline, m.p. 103° C. (hexane), (Example 36);

(RS)-1-(4-[1,2,4]triazol-1-ylmethyl-phenyl)-1,2,3,4-tetrahydro-isoquinoline, m.p. 96°–98° C. (ethyl acetate/hexane), (Example 54);

(RS)-1-(4-methylsulphanyl-phenyl)-1,2,3,4-tetrahydro-isoquinoline, m.p. 94° C. (diisopropyl ether), (Example 55);

(RS)-1-(3-methanesulphonyl-phenyl)-1,2,3,4-tetrahydro-isoquinolin, b.p. 250° C./0.15 mbar (bulb-tube), (Example 56);

(RS)-1-(6-methylsulphanyl-pyridin-3-yl)-1,2,3,4-tetrahydro-isoquinoline, m.p. 86° C. (isopropanol), (Example 57);

(RS)-2-{ methyl-[5-(1,2,3,4-tetrahydro-isoquinolin-1-yl)-pyridin-2-yl]-amino}-ethanol, MS (EI): 283M$^{30}$, (Example 58).

c) A solution of 9.08 g of 1-(2,5-dimethyl-2H-pyrazol-3-yl)-3,4-dihydro-isoquinoline in 400 ml of abs. methanol was treated at room temperature with a spatula tip of bromocresol green as well as 2.79 g of sodium cyanoborohydride. A pH of 4–6 was maintained during the entire reaction period by the addition of HCl gas dissolved in abs. methanol (about 2N). After 2.5 h., the solvent was distilled off on a rotary evaporator, the residue was taken up in ethyl acetate and washed with semi-saturated sodium bicarbonate solution. Re-extraction of the aqueous phase with ethyl acetate, washing of the combined organic phases with sat. aqueous sodium chloride solution, drying over sodium sulfate and evaporation gave 9.22 g of a brown oil which was purified over silica gel with ethyl acetate/methanol 75:25. There were obtained 7.44 g (81%) of (RS)-1-(2,5-dimethyl-2H-pyrazol-3-yl)-1,2,3,4-tetrahydro-isoquinoline as a yellow oil. MS (EI): 227M$^{30}$.

The following compounds were obtained in analogy to the preparation of (RS)-1-(2,5-dimethyl-2H-pyrazol-3-yl)-1,2,3,4-tetrahydro-isoquinoline described under Cc):

(RS)-1-(2-Methyl-4-morpholin-4-ylmethyl-2H-pyrazol-3-yl)-1,2,3,4-tetrahydro-isoquinoline, colorless oil, MS (TSP): 312M$^{30}$, (Example 62);

(RS)-1-[1-methyl-5-(4-methyl-piperazin-1-ylmethyl)-1H-pyrazol-3-yl]-1,2,3,4-tetrahydro-isoquinoline, yellowish oil, b.p. 190°–195° C./0.15 mbar (bulb-tube), (Example 63);

(RS)-1-(4-methyl-[1,2,3]thiadiazol-5-yl)-1,2,3,4-tetrahydro-isoquinoline, m.p. 85°–86° C. (digestion in pentane), (Example 72);

(RS)-1-(1H-[1,2,4]triazol-3-yl)-1,2,3,4-tetrahydro-isoquinoline, m.p. 172°–173° C. (isopropanol), (Example 73);

(RS)-1-(5-methyl-1H-imidazol-4-yl)-1,2,3,4-tetrahydro-isoquinoline, m.p. 179°–180° C. (isopropanol), (Example 74);

(RS)-1-(5-pyridin-2-yl-thiophen-2-yl)-1,2,3,4-tetrahydro-isoquinoline, m.p. 111°–112° C. (tert.-butyl methyl ether), (Example 75);

(RS)-1-(5-furan-2-yl-thiazol-4-yl)-1,2,3,4-tetrahydro-isoquinoline, dark red resin, MS (EI): 282M$^{30}$, (Example 76);

(RS)-1-(1-benzyl-5-methyl-1H-pyrazol-3-yl)-1,2,3,4-tetrahydro-isoquinoline, colorless oil, MS (ISP): 304.3 (M+H)$^+$, Example 77);

(RS)-1-(5-methyl-2H-pyrazol-3-yl)-1,2,3,4-tetrahydro-isoquinoline, beige foam, MS (EI): 213M$^+$, (Example 78);

(RS)-1-(2-pyridin-3-yl-thiazol-4-yl)-1,2,3,4-tetrahydro-isoquinoline, yellowish oil, MS (EI): 293M$^{30}$, (Example 79);

(RS)-dimethyl-[1-methyl-4-(1,2,3,4-tetrahydro-isoquinolin-1-yl)-1H-pyrazol-3-yl)-amine, yellow oil, MS (ISP): 257.5 (M+H)$^+$, (Example 80).

d) (RS)-[4-(1,2,3,4-Tetrahydro-isoquinolin-1-yl)-phenyl]-methanol, m.p. 1380C. (ethanol), was prepared by reducing ethyl 4- (1,2,3,4-tetrahydro-isoquinolin-1-yl)-benzoate with lithium aluminium hydride in tetrahydrofuran at 0° C. (Example 60).

(RS)-2-[1-Methyl-5-(1,2,3,4-tetrahydro-isoquinolin-1-yl)-1H-pyrazol-3-yl]-ethanol, yellowish oil, MS (ISP): 258.3 (M+H)$^+$, (Example 68);

(RS)-[1-methyl-5-(1,2,3,4-tetrahydro-isoquinolin-1-yl)-1H-pyrazol-3-yl]-methanol, yellow foam, MS (ISP): 244.2 (M+H)$^+$, (Example 70).

D. 1-(3.4-Dihydro-1H-isoquinolin-2-yl)-propenone derivatives (compounds of formula III)

A solution of 2.44 ml of acryloyl chloride in 5 ml of toluene was added dropwise while stirring and cooling with ice within 15 min. to 6.2 g of (R)-1-pyridin-2-yl-1,2,3,4-tetrahydro-isoquinoline and 5 ml of triethylamine in 80 ml of toluene. After stirring at room temperature for a further 10 min., the mixture was treated with 100 ml of water and extracted with 2×80 ml of diethyl ether. The combined organic phases were washed with 50 ml of water, dried over sodium sulfate and evaporated to dryness. There were obtained 8.07 g of (R)-1-(1-pyridin-2-yl-3,4-dihydro-1H-isoquinolin-2-yl)-propenone as a viscous resin, b.p. 180° C./0.1 mbar.

The following compounds were obtained in analogy to the preparation of (R)-1-(1-pyridin-2-yl-3,4-dihydro-1H-isoquinolin-2-yl)-propenone described under D.:

1-(3,4-Dihydro-1H-isoquinolin-2-yl)-propenone, b.p. 160° C./1.5 mbar, (Example 2);

(RS)-1-(1-pyridin-2-yl-3,4-dihydro-1H-isoquinolin-2-yl)-propenone, b.p. about 180° C./0.8 mbar, (Example 3);

1-(7-chloro-3,4-dihydro-1H-isoquinolin-2-yl)-propenone, b.p. about 170° C./0.1 mbar, (Example 4);

(RS)-1-(1-phenyl-3,4-dihydro-1H-isoquinolin-2-yl)-propenone, b.p. about 175° C./0.1 mbar, (Example 5);

(RS)-1-(1-pyridin-4-yl-3,4-dihydro-1H-isoquinolin-2-yl)-propenone, b.p. 250° C./0.2 mbar, (Example 6);

(RS)-1-(1-pyridin-3-yl-3,4-dihydro-1H-isoquinolin-2-yl)-propenone, m.p. 83° C. (diisopropyl ether), (Example 7);

(RS)-1-(7-methoxy-1-pyridin-2-yl-3,4-dihydro-1H-isoquinolin-2-yl)-propenone, b.p. 240° C./0.12 mbar, (Example 8);

(RS)-1-(1-pyrazin-2-yl-3,4-dihydro-1H-isoquinolin-2-yl)-propenone, m.p. 95°–97° C. (toluene/hexane), (Example 10);

(RS)-1-(7-chloro-1-pyridin-2-yl-3,4-dihydro-1H-isoquinolin-2-yl)-propenone, b.p. 220° C./0.06 mbar, (Example 11);

(RS)-1-(7-methyl-1-pyridin-2-yl-3,4-dihydro-1H-isoquinolin-2-yl)-propenone, b.p. 190° C./0.05 mbar, (Example 12);

(RS)-1-[1-(4-chloro-phenyl)-3,4-dihydro-1H-isoquinolin-2-yl]-propenone, b.p. 190° C./0.2 mbar, (Example 13);

(RS)-1-(1-cyclohexyl-3,4-dihydro-1H-isoquinolin-2-yl)-propenone, b.p. 250° C./0.15 mbar, (Example 14);

(RS)-1-(1-pyrimidin-5-yl-3,4-dihydro-1H-isoquinolin-2-yl)-propenone, MS (EI): 265M$^{30}$, (Example 15);

(RS)-1-[1-(4-methyl-phenyl)-3,4-dihydro-1H-isoquinolin-2-yl]-propenone, b.p. 190° C./0.2 mbar, (Example 16);

(RS)-1-(1-pyrimidin-4-yl-3,4-dihydro-1H-isoquinolin-2-yl)-propenone, MS (ISP): 266.4 (M+H)$^+$, (Example 17);

(RS)-1-(1-benzyl-3,4-dihydro-1H-isoquinolin-2-yl)-propenone, oil, (Example 18);

(RS)-1-(1-isobutyl-3,4-dihydro-1H-isoquinolin-2-yl)-propenone, b.p. 200° C./0.3 mbar, (Example 19);

(RS)-1-[1-(4-methoxy-phenyl)-3,4-dihydro-1H-isoquinolin-2-yl]-propenone, b.p. about 200° C./0.08 mbar, (Example 20);

(RS)-1-(1-cyclopropyl-3,4-dihydro-1H-isoquinolin-2-yl)-propenone, b.p. 200° C./0.3 mbar, (Example 22);

(RS)-4-(2-acryloyl-1,2,3,4-tetrahydro-isoquinolin-1-yl)-benzonitrile, b.p. 220° C./0.1 mbar, (Example 23);

(RS)-1-[1-(4-dimethylamino-phenyl)-3,4-dihydro-1H-isoquinolin-2-yl]-propenone, b.p. about 180° C./0.08 mbar, (Example 24);

(RS)-1-(1-pyridazin-3-yl-3,4-dihydro-1H-isoquinolin-2-yl)-propenone, MS (EI): 265M$^{30}$, (Example 25);

(RS)-1-(1-pyridazin-4-yl-3,4-dihydro-1H-isoquinolin-2-yl)-propenone, MS (EI): 265M$^{30}$, (Example 26);

(RS)-1-(1-thiophen-2-yl-3,4-dihydro-1H-isoquinolin-2-yl)-propenone, m.p. 110° C. (diisopropyl ether), (Example 27);

(RS)-2-acryloyl-1,2,3,4-tetrahydro-isoquinolin-1-carbonitrile, m.p. 101°–104° C. (ethanol), (Example 28);

(RS)-1-(1-(4-trifluoromethyl-phenyl)-3,4-dihydro-1H-isoquinolin-2-yl)-propenone, b.p. 180° C./0.07 mbar, (Example 29);

(RS)-1-[1-(6-hydroxy-pyridin-3-yl)-3,4-dihydro-1H-isoquinolin-2-yl]-propenone, oil, (Example 30);

ethyl (RS)-4-(2-acryloyl-1,2,3,4-tetrahydro-isoquinolin-1-yl)-benzoate, b.p. about 220° C./0.1 mbar, (Example 31);

(RS)-1-[1-(6-methyl-pyridin-3-yl)-3,4-dihydro-1H-isoquinolin-2-yl]-propenone, oil, MS (ISP): 279.4 (M+H)$^+$, (Example 32);

(RS)-1-[1-(6-chloro-pyridin-3-yl)-3,4-dihydro-1H-isoquinolin-2-yl]-propenone, oil, MS (EI): 298M$^{30}$, (Example 36);

(RS)-1-[1-(4-chloro-pyridin-2-yl)-3,4-dihydro-1H-isoquinolin-2-yl]-propenone, b.p. about 180° C./0.1 mbar, (Example 33);

(RS)-1-(1-(5-chloro-pyridin-2-yl)-3,4-dihydro-1H-isoquinolin-2-yl)-propenone, b.p. about 195° C./0.065 mbar, (Example 34);

(RS)-1-[1-(6-dimethylamino-pyridin-3-yl)-3,4-dihydro-1H-isoquinolin-2-yl]-propenone, m.p. 125°–126° C. (hexane), (Example 35);

(RS)-1-[1-(4-diethylaminomethyl-phenyl)-3,4-dihydro-1H-isoquinolin-2-yl]-propenone, oil, (Example 38);

(R,S)-5-(2-acryloyl-1,2,3,4-tetrahydro-isoquinolin-1-yl)-pyridine-2-carboxamide, MS (ISP): 308.3 (M+H)$^+$, (Example 39:);

1-[1-(4-methanesulphonyl-phenyl)-3,4-dihydro-1H-isoquinolin-2-yl]-propenone, resin, (Example 40);

(RS)-1-[1-(2,5-dimethyl-2H-pyrazol-3-yl)-3,4-dihydro-1H-isoquinolin-2-yl]-propenone, m.p. 125°–126.5° C., (Example 41);

(RS)-1-[1-(4-methyl-[1,2,3]thiadiazol-5-yl)-3,4-dihydro-1H-isoquinolin-2-yl]-propenone, m.p. 136°–137° C., (Example 42);

(RS)-1-(1H-[1,2,4]triazol-3-yl)-3,4-dihydro-1H-isoquinolin-2-yl]-propenone, colourless foam, MS (ISP): 255.4 (M+H)$^+$, (Example 43);

(RS)-1-[1-(5-methyl-1H-imidazol-4-yl)-3,4-dihydro-1H-isoquinolin-2-yl]-propenone, m.p. 159°–160° C. (ethyl acetate), (Example 44);

(RS)-1-[1-(5-pyridin-2-yl-thiophen-2-yl)-3,4-dihydro-1H-isoquinolin-2-yl]-propenone, yellow foam, MS (EI): 346M$^{30}$, (Example 45);

(RS)-1-[1-(5-furan-2-yl-thiazol-4-yl)-3,4-dihydro-1H-isoquinolin-2-yl]-propenone, red resin, MS (EI): 336M$^{30}$, (Example 46);

(RS)-1-[1-(1-benzyl-5-methyl-1H-pyrazol-3-yl)-3,4-dihydro-1H-isoquinolin-2-yl]-propenone, colourless oil, MS (EI): 357M$^{30}$, (Example 47);

(RS)-1-[1-(5-methyl-2H-pyrazol-3-yl)-3,4-dihydro-1H-isoquinolin-2-yl]-propenone, colourless foam, MS (EI): 267M$^+$, (Example 48);

(RS)-1-[1-(2-pyridin-3-yl-thiazol-4-yl)-3,4-dihydro-1H-isoquinolin-2-yl]-propenone, m.p. 111.5°–114° C. (ethyl acetate/pentane 1:1), (Example 49);

(RS)-1-(1-(3-dimethylamino-1-methyl-1H-pyrazol-4-yl)-3,4-dihydro-1H-isoquinolin-2-yl)-propenone, m.p. 93°–95° C. (tert.-butyl methyl ether/pentane 1:1), (Example 50);

(RS)-1-[1-(4-imidazol-1-yl-phenyl)-3,4-dihydro-1H-isoquinolin-2-yl]-propenone, (Example 51);

(RS)-1-[1-(4-imidazol-1-ylmethyl-phenyl)-3,4-dihydro-1H-isoquinolin-2-yl]-propenone, (Example 52);

(RS)-1-[1-(4-[1,2,4]triazol-1-yl-phenyl)-3,4-dihydro-1H-isoquinolin-2-yl]-propenone, (Example 53);

(RS)-1-[1-(4-[1,2,4]triazol-1-ylmethyl-phenyl)-3,4-dihydro-1H-isoquinolin-2-yl]-propenone, MS (ISP): 345.2 (M+H)$^+$, (Example 54);

(RS)-1-[1-(4-methylsulphanyl-phenyl)-3,4-dihydro-1H-isoquinolin-2-yl]-propenone, MS (EI): 309M$^{30}$, (Example 55);

(RS)-1-[1-(3-methanesulphonyl-phenyl)-3,4-dihydro-1H-isoquinolin-2-yl]-propenone, MS (EI): 341M$^{30}$, (Example 56);

(RS)-1-[1-(6-methylsulphanyl-pyridin-3-yl)-3,4-dihydro-1H-isoquinolin-2-yl]-propenone, MS (ISP): 311.2 (M+H)$^+$, (Example 57);

(RS)-1-(1-{6-[(2-hydroxy-ethyl)-methyl-amino]-pyridin-3-yl}-3,4-dihydro-1H-isoquinolin-2-yl)-propenone, MS (ISP): 338.2 (M+H)$^+$, (Example 58);

(RS)-1-(1-methyl-3,4-dihydro-1H-isoquinolin-2-yl)-propenone, MS (EI): 201M$^{30}$, (Example 59);

(RS)-1-[1-(4-hydroxymethyl-phenyl)-3,4-dihydro-1H-isoquinolin-2-yl]-propenone, MS (EI): 293M$^{30}$, (Example 60);

(RS)-1-(1-ethyl-3,4-dihydro-1H-isoquinolin-2-yl)-propenone, b.p. 150° C./0.3 mbar (bulb-tube), (Example 61);

(RS)-1-[1-(2-methyl-4-morpholin-4-ylmethyl-2H-pyrazol-3-yl)-3,4-dihydro-1H-isoquinolin-2-yl]-propenone, m.p. 127.5°–130° C., (Example 62);

(RS)-1-[1-[1-methyl-5-(4-methyl-piperazin-1-ylmethyl)-1H-pyrazol-3-yl]-3,4-dihydro-1H-isoquinolin-2-yl]-propenone, oil, MS (ISP): 380.4 (M+H)$^+$, (Example 63);

(RS)-1-[1-(2,5-dimethyl-2H-pyrazol-3-yl)-3,4-dihydro-1H-isoquinolin-2-yl]-propenone, m.p. 125°–126.5° C., (Example 71);

(RS)-1-[1-(4-methyl-[1,2,3]thiadiazol-5-yl)-3,4-dihydro-1H-isoquinolin-2-yl]-propenone, m.p. 136°–137° C., (Example 72);

(RS)-1-(1H-[1,2,4]triazol-3-yl)-3,4-dihydro-1H-isoquinolin-2-yl]-propenone, colourless foam, MS (ISP): 255.4 (M+H)⁺, (Example 73);

(RS)-1-[1-(5-methyl-1H-imidazol-4-yl)-3,4-dihydro-1H-isoquinolin-2-yl]-propenone, m.p. 159°–160° C. (ethyl acetate), (Example 74);

(RS)-1-[1-(5-pyridin-2-yl-phen-2-yl)-3,4-dihydro-1H-isoquinolin-2-yl]-propenone, yellow foam, MS (EI): 346M³⁰, (Example 75);

(RS)-1-[1-(5-furan-2-yl-thiazol-4-yl)-3,4-dihydro-1H-isoquinolin-2-yl]-propenone, red resin, MS (EI): 336M³⁰, (Example 76);

(RS)-1-[1-(1-benzyl-5-methyl-1H-pyrazol-3-yl)-3,4-dihydro-1H-isoquinolin-2-yl]-propenone, colourless oil, MS (EI): 357M³⁰, (Example 77);

(RS)-1-[1-(5-methyl-2H-pyrazol-3-yl)-3,4-dihydro-1H-isoquinolin-2-yl]-propenone, colourless foam, MS (EI): 267M³⁰, (Example 78);

(RS)-1-[1-(2-pyridin-3-yl-thiazol-4-yl)-3,4-dihydro-1H-isoquinolin-2-yl]-propenone, m.p. 111.5°–114° C. (ethyl acetate/pentane 1:1), (Example 79);

(RS)-1-[1-(3-dimethylamino-1-methyl-1H-pyrazol-4-yl)-3,4-dihydro-1H-isoquinolin-2-yl]-propenone, m.p. 93°–95° C. (tert.-butyl methyl ether/pentane 1:1), (Example 80).

The following compounds were obtained by reaction with acryloyl chloride in dichloromethane at ≦–50° C:

(RS)-1-[1-(1-Methyl-4-morpholin-4-ylmethyl-1H-pyrazol-3-yl)-3,4-dihydro-1H-isoquinolin-2-yl]-propenone, m.p. >106° C. dec.7 (tert.-butyl methyl ether), (Example 64);

(RS)-1-[1-(2-methyl-5-morpholin-4-ylmethyl-2H-pyrazol-3-yl)-3,4-dihydro-1H-isoquinolin-2-yl]-propenone, m.p. 162°–165° C. (tert.-butyl methyl ether), (Example 65);

(RS)-2-[5-(2-acryloyl-1,2,3,4-tetrahydro-isoquinolin-1-yl)-1-methyl-1H-pyrazol-3-yl]-acetamide, m.p. 168°–170° C., (Example 66);

(RS)-1-[1-(1-methyl-5-morpholin-4-ylmethyl-1H-pyrazol-3-yl)-3,4-dihydro-1H-isoquinolin-2-yl]-propenone, yellow oil, MS (ISP): 367.3 (M+H)⁺, (Example 67);

(RS)-1-[1-[5-(2-hydroxy-ethyl)-2-methyl-2H-pyrazol-3-yl]-3,4-dihydro-1H-isoquinolin-2-yl]-propenone, m.p. 133°–134° C. (acetonitrile), (Example 68);

methyl (RS)-[5-(2-acryloyl-1,2,3,4-tetrahydro-isoquinolin-1-yl)-1-methyl-1H-pyrazol-3-yl]-acetate, m.p. 128°–129° C. (ethyl acetate), (Example 69);

(RS)-1-[1-(5-hydroxymethyl-2-methyl-2H-pyrazol-3-yl)-3,4-dihydro-1H-isoquinolin-2-yl]-propenone, m.p. 134°–136° C. (digestion in pentane), (Example 70).

E. 1-(3.4-Dihydro-1H-isoquinolin-2-yl)-propynone derivatives (compounds of formula III: Q=ethynylene)

(i) A solution of 1.47 g of bis(trichloromethyl) carbonate in 10 ml of methylene chloride was added dropwise within 20 min. to a solution of 2 g of 1,2,3,4-tetrahydro-isoquinoline in 30 ml of methylene chloride and 2.5 ml of triethylamine under argon at 0° C. The reaction mixture was stirred at room temperature for 2 h., then diluted with 50 ml of methylene chloride and washed with 50 ml of water, 50 ml of a 5% hydrochloric acid solution, 50 ml of a saturated sodium hydrogen carbonate solution and 50 ml of a saturated sodium chloride solution. The organic phases were dried over magnesium sulfate, concentrated, and the residue was dried at room temperature and about 12 mbar. 2.74 g (94%) of 3,4-dihydro-1H-isoquinoline-2-carbonyl chloride were obtained as a pale orange oil. MS (EI): 195M³⁰.

(ii) A solution of 2.73 g of 3,4-dihydro-1H-isoquinoline-2-carbonyl chloride, 55 mg of 4-dimethylamino-pyridine, 1.36 g of N,O-dimethylhydroxylamine hydrochloride and 4.85 ml of triethylamine in 30 ml of methylene chloride was heated to boiling under reflux for 22 h. The reaction mixture was treated at room temperature with 50 ml of a 5% sodium carbonate solution and extracted twice with 50 ml of methylene chloride each time. The combined organic phases were washed once with 50 ml of water and once with 50 ml of a saturated sodium chloride solution, dried over magnesium sulfate and concentrated. The residue was triturated with 50 ml of t-butyl methyl ether, a small amount of insoluble residue was filtered off under suction and the filtrate was concentrated. The residue was dried at room temperature and about 12 mbar. 2.87 g (93%) of 3,4-dihydro-1H-isoquinoline-2-carboxylic acid methoxy-methyl-amide were obtained as an orange oil. MS (EI): 220M³⁰.

(iii) 9.08 ml of a 0.5 molar solution of ethynylmagnesium bromide in tetrahydrofuran were added dropwise within 20 min. to a solution of 1 g of 3,4-dihydro-1H-isoquinoline-2-carboxylic acid methoxy-methyl-amide in 5 ml of tetrahydrofuran under argon at 0° C. The reaction mixture was stirred at 0° C. for 1 h. and at room temperature for 1 h. The orange solution was poured into 50 ml of a saturated ammonium chloride solution and extracted twice with 50 ml of ethyl acetate each time. The combined organic phases were washed twice with 50 ml of water each time, once with 50 ml of a saturated sodium chloride solution, dried over magnesium sulfate and concentrated. 0.48 g (57%) of 1-(3,4-dihydro-1H-isoquinolin-2-yl)-propynone was obtained as a yellowish oil. MS (EI): 185M³⁰.

F. Preparation of the carboxylic acid phenethylamide derivatives used in A.

Educt for Example 62 i) Ethyl 4-hydroxymethyl-2-methyl-2H-pyrazole-3-carboxylate, colorless oil, MS (TSP): 184M³⁰, was prepared by reacting ethyl 4-hydroxymethyl-1H-pyrazole-3-carboxylate, m.p. 119°–121° C., with methyl iodide and potassium carbonate in acetone at room temperature for 2 hours.

(ii) Ethyl 4-bromomethyl-2-methyl-2H-pyrazole-3-carboxylate, colourless oil, MS (TSP): 246 and 248M³⁰, was prepared by reacting ethyl 4-hydroxymethyl-2-methyl-2H-pyrazole-3-carboxylate with tetrabromomethane and triphenylphosphine in diethyl ether at room temperature for 22 hours.

iii) Ethyl 2-methyl-4-morpholin-4-ylmethyl-2H-pyrazole-3-carboxylate, semi-crystalline, colourless product, MS (TSP): 253 M⁺, was prepared by reacting ethyl 4-bromomethyl-2-methyl-2H-pyrazol-3-carboxylate with morpholine in acetone at room temperature for 1.5 hours.

The following compounds were prepared in an analogous manner:

Educt for Example 63 i) Ethyl 5-hydroxymethyl-1-methyl-1H-pyrazole-3-carboxylate, colorless oil; b.p. 140°–145° C./0.18 mbar (bulb-tube), was prepared by reacting ethyl 5-hydroxymethyl-1H-pyrazole-3-carboxylate, m.p. 92°–93° C., with methyl iodide and potassium carbonate in acetone at room temperature for 2 hours.

(ii) Ethyl 5-bromomethyl-1-methyl-1H-pyrazol-3-carboxylate, m.p. 68.5°–69.5° C., was prepared by reacting ethyl 5-hydroxymethyl-1-methyl-1H-pyrazole-3-carboxylate with tetrabromomethane and triphenylphosphine in diethyl ether at room temperature for 17 hours.

(iii) Ethyl 1-methyl-5-(4-methyl-piperazin-1-ylmethyl)-1H-pyrazole-3-carboxylate, yellow oil, MS (EI): 266M³⁰, was prepared by reacting ethyl 5-bromomethyl-1-methyl-1H- pyrazole-3-carboxylate with 1-methylpiperazine in acetone at room temperature for 3 hours.

Educt for Example 64 i) Ethyl 4-hydroxymethyl-1-methyl-1H-pyrazole-3-carboxylate, m.p. 73°–75° C., was prepared by reacting ethyl 4-hydroxymethyl-1H-pyrazole-3-carboxylate, m.p. 119°–121° C., with methyl iodide and potassium carbonate in acetone at room temperature for 2 hours.

ii) Ethyl 4-bromomethyl-1-methyl-1H-pyrazole-3-carboxylate, m.p. 112°–114° C., was prepared by reacting ethyl 4-hydroxymethyl-1-methyl-1H-pyrazole-3-carboxylate with tetrabromomethane and triphenylphosphine in a diethyl ether/monoglyme mixture at room temperature for 4 days.

(iii) Ethyl 1-methyl-4-morpholin-4-ylmethyl-1H-pyrazole-3-carboxylate, yellowish oil, MS (ISP): 254.3 (M+H)$^+$, was prepared by reacting ethyl 4-bromomethyl-1-methyl-1H-pyrazole-3-carboxylate with morpholine in acetone at room temperature for 30 minutes.

Educt for Example 65 i) Ethyl 5-hydroxymethyl-2-methyl-2H-pyrazole-3-carboxylate, colorless oil, b.p. 100°–105° C./0.15 mbar (bulb-tube), was prepared by reacting ethyl 5-hydroxymethyl-1H-pyrazole-3-carboxylate, m.p. 92°–93° C., with methyl iodide and potassium carbonate in acetone at room temperature for 2 hours.

ii) Ethyl 5-bromomethyl-2-methyl-2H-pyrazole-3-carboxylate, m.p. 69°–71° C., was prepared by reacting ethyl 5-hydroxymethyl-2-methyl-2H-pyrazole-3-carboxylate with tetrabromomethane and triphenylphosphine in diethyl ether at room temperature for 28 hours.

iii) Ethyl 2-methyl-5-morpholin-4-ylmethyl-2H-pyrazole-3-carboxylate, brown oil, MS (TSP): 253M$^{30}$, was prepared by reacting ethyl 5-bromomethyl-2-methyl-2H-pyrazole-3-carboxylate with morpholine in acetone at room temperature for 1 hour.

Educts for Examples 66 and 67 i) A mixture of ethyl 5-methoxymethyl-1-methyl-1H-pyrazole-3-carboxylate and ethyl 5-methoxymethyl-2-methyl-2H-pyrazole-3-carboxylate, yellow oil, MS (EI): 198.1M$^{30}$, was obtained by methylating a mixture of ethyl 5-hydroxymethyl-2-methyl-2H-pyrazole-3-carboxylate and ethyl 5-hydroxymethyl-1-methyl-1H-pyrazole-3-carboxylate with NaH and methyl iodide in DMF.

ii) A 1:1 mixture of 5-hydroxymethyl-1-methyl-1H-pyrazole-3-carboxylic acid phenethyl-amide and 5-hydroxymethyl-2-methyl-2H-pyrazole-3-carboxylic acid phenethyl-amide, yellow oil, MS (EI): 259.1M$^{30}$, was prepared analogously to Ac) from a mixture of ethyl 5-methoxymethyl-1-methyl-1H-pyrazole-3-carboxylate and ethyl 5-methoxymethyl-2-methyl-2H-pyrazole-3-carboxylate. Chromatographic separation on silica gel yielded not only the desired product, but also the isomeric 5-bromo-methyl-1-methyl-1H-pyrazole-3-carboxylic acid phenethyl-amide, yellow oil, MS (EI): 321 and 323M$^{30}$.

iii) 5-Bromomethyl-2-methyl-2H-pyrazole-3-carboxylic acid phenethyl-amide, m.p. 112°–113° C., was obtained by reacting a 1:1 mixture of 5-hydroxymethyl-1-methyl-1H-pyrazole-3-carboxylic acid phenethylamide and 5-hydroxymethyl-2-methyl-2H-pyrazole-3-carboxylic acid phenethylamide with tetrabromo-methane and triphenylphosphine in ethyl acetate at room temperature for 21 hours and subsequently separating the mixture obtained by chromatography.

Educt for Example 70

Ethyl 1-methyl-1H-pyrazole-3,5-dicarboxylic acid 3-ethyl ester, m.p. 128°–129° C., was prepared by oxidizing ethyl 5-hydroxymethyl-1-methyl-1H-pyrazole-3-carboxylate with sodium periodate and a catalytic amount of ruthenium trichloride in a mixture of CCl$_4$/MeCN/H$_2$O at 20°–40° C. for 1.5 hours.

Pharmaceutical preparations can be produced in a manner known per se in accordance with the following formulations:

| Example A | |
|---|---|
| Tablets | |
| Sulfamethoxazole | 400 mg |
| Compound of formula I, for example, (E)-(R)-3-[5-(2,4-diamino-pyrimidin-5-ylmethyl)-2,3-dimethoxyphenyl]-1-(1-pyridin-2-yl-3,4-dihydro-1H-isoquinolin-2-yl)-propenone | 80 mg |
| PRIMOJEL (starch derivative) | 6 mg |
| POVIDONE K30 (polyvinylpyrrolidone) | 8 mg |
| Magnesium stearate | 6 mg |
| Total weight | 500 mg |

| Example B | |
|---|---|
| Tablets | |
| Compound of formula I, for example, (E)-(R)-3-[5-(2,4-diamino-pyrimidin-5-ylmethyl)-2,3-dimethoxy-phenyl]-1-(1-pyridin-2-yl-3,4-dihydro-1H-isoquinolin-2-yl)-propenone | 100 mg |
| Corn starch | 15 mg |
| Talc | 3 mg |
| Magnesium stearate | 2 mg |
| | 120 mg |

| Example C | |
|---|---|
| Injection solutions: | |
| Compound of formula I, for example, (E)-(R)-3-[5-(2,4-diamino-pyrimidin-5-ylmethyl)-2,3-dimethoxy-phenyl]-1-(1-pyridin-2-yl-3,4-dihydro-1H-isoquinolin-2-yl)-propenone | 5 mg |
| Glycofurol 75 | 0.2 ml |
| Bidistilled sterile water | ad 1.0 ml |

| Example D | |
|---|---|
| Injection solutions: | |
| Compound of formula I, for example, (E)-(R)-3-[5-(2,4-diamino-pyrimidin-5-ylmethyl)-2,3-dimethoxy-phenyl]-1-(1-pyridin-2-yl-3,4-dihydro-1H-isoquinolin-2-yl)-propenone | 5 mg |
| Propylene glycol | 0.5 ml |
| Bidistilled sterile water | ad 1.0 ml |

We claim:

1. A compound of the formula:

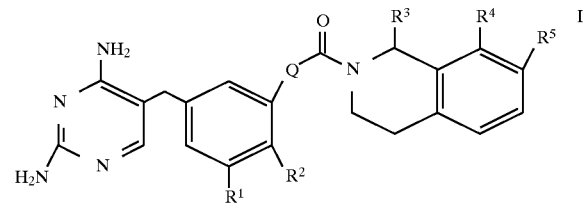

wherein
R$^1$ is C$_1$–C$_6$ alkoxy;
R$^2$ is bromine, C$_1$–C$_6$ alkoxy, or hydroxy;
R$^3$ is hydrogen, C$_1$–C$_6$ alkyl, cycloalkyl, aryl, heterocyclyl, aralkyl, heterocyclyl C$_1$–C$_6$ alkyl, or cyano,
  wherein aryl is selected from the group consisting of phenyl; phenyl substituted with phenyl, C$_1$–C$_6$ alkyl, C$_3$–C$_6$ cycloalkyl, halogen, trifluoromethyl, C$_1$–C$_6$ alkoxy, C$_1$–C$_6$ alkoxy-carbonyl, hydroxy, di(C$_1$–C$_6$ alkyl) amino, cyano, carbamoyl, mono-(C$_1$–C$_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; naphthyl; naphthyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-( $C_1$–$C_6$ alkyl)sulfamoyl, or di-($C_1$–$C_6$ alkyl)sulfamoyl; anthryl; anthryl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; phenanthryl; phenanthryl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; 2H-tetrazol-5-yl-phenyl; 4-morpholin-4-yl-methyl-phenyl; 4-methyl-piperazin-1-yl-methyl-phenyl; 4-imidazo-1-yl-phenyl; 4-imidazo-1-yl-methyl-phenyl; triazol-1-yl-phenyl; and 1,2,4-triazol-1-yl-methyl-phenyl; and heterocyclyl is selected from the group consisting of furyl; furyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyranyl; pyranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-( $C_1$–$C_6$ alkyl)sulfamoyl, or di-($C_1$–$C_6$ alkyl)sulfamoyl; thienyl; thienyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyrrolyl; pyrrolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-( $C_1$–$C_6$ alkyl)sulfamoyl, or di-($C_1$–$C_6$ alkyl)sulfamoyl; pyrazolyl; pyrazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; imidazolyl; imidazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-( $C_1$–$C_6$ alkyl) sulfamoyl, or di-($C_1$–$C_6$ alkyl)sulfamoyl; thiazolyl; thiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; tetrazolyl; tetrazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-( $C_1$–$C_6$ alkyl)sulfamoyl, or di-($C_1$–$C_6$ alkyl)sulfamoyl; oxazolyl; oxazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; oxadiazolyl; oxadiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; isoxazolyl; isoxazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-( $C_1$–$C_6$ alkyl)sulfamoyl, or di-($C_1$–$C_6$ alkyl)sulfamoyl; thiazolyl; thiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl or di-($C_1$–$C_6$ alkyl)sulfamoyl; isothiazolyl; isothiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyridyl; pyridyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-( $C_1$–$C_6$ alkyl) sulfamoyl, or di-($C_1$–$C_6$ alkyl)sulfamoyl; pyridazinyl; pyridazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyrimidinyl; pyrimidinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyrazinyl; pyrazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; triazinyl; triazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; benzopyranyl; benzopyranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; benzofuranyl; benzofuranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; indolyl; indolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; quinolinyl; quinolinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; 2-pyridin-3-yl-thiazol; 1-benzyl-5-methyl-1H-pyrazol-3-yl; 5-furan-2-yl-thiazol-4-yl; 5-pyridin-2-yl-thiophen-2-yl; 6-morpholin-4-yl-pyridin-3-yl; 4-methyl-piperazin-1-yl-pyridin-3-yl; 4-methyl-piperazin-1-yl-methyl-1H-pyrazol-3-yl; 2-methyl-4-morpholin-4-yl-methyl-2H-pyrazol-3-yl; morpholin-4-yl; 4-methyl-piperazin-1-yl; imidazol-1-yl; [1,2,4]triazol-1-yl; tetrazol; morpholin-4-yl-methyl; 4-methyl-piperazin-1-yl-methyl imidazol-1-yl-methyl; [1,2,4]triazol-1-yl-methyl; and cyclo($C_3$–$C_6$ alkyl)amino;

$R^4$ is hydrogen, $C_1$–$C_6$ alkyl, $C_1$–$C_6$ alkoxy, halogen, hydroxy, amino, di($C_1$–$C_6$ alkyl)amino, cyano, or nitro;

$R^5$ is hydrogen, $C_1$–$C_6$ alkyl, $C_1$–$C_6$ alkoxy, halogen, hydroxy, amino, di($C_1$–$C_6$ alkyl)amino, cyano, or nitro; and Q is ethynyene or vinylene;

or a pharmaceutically usable salt thereof.

2. A compound according to claim 1, wherein $R^1$ and $R^2$ $C_1$–$C_6$ alkoxy, $R^3$ is phenyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyridyl, or thienyl; $R^4$ is hydrogen; and $R^5$ is hydrogen or $C_1$–$C_6$ alkoxy.

3. The compound according to claim 2, wherein $R^1$ and $R^2$ are methoxy.

4. The compound according to claim 1, wherein $R^3$ is 2-pyridyl, 3-pyridyl, or pyridyl substituted with phenyl, $C_{1-6}$ alkyl, $C_3$–$C_6$ cycloalkyl, halogen, trifluoromethyl $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$alkyl) carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl.

5. The compound according to claim 2, wherein $R^5$ is methoxy.

6. The compound according to claim 1, wherein Q is vinylene.

7. The compound according to claim 2, wherein Q is vinylene.

8. The compound of claim 1 which is (E)-(RS)-3-[5-(2,4-diamino-pyrimidin-5-ylmethyl)-2,3-dimethoxy-phenyl]-1-[1-(2,5-dimethyl-2H-pyrazol-3-yl)-3,4-dihydro-1H-1isoquinolin-2-yl]-propenone.

9. The compound of claim 1 which is (E)-(RS)-1-(1-cyclopropyl-3,4-dihydro-1H-1isoquinolin-2-yl)-3-[5-(2,4-diamino-pyrimidin-5-ylmethyl)-2,3-dimethoxy-phenyl]-propenone.

10. The compound of claim 1 which is (E)-(RS)-3-[5-(2,4-diamino-pyrimidin-5-ylmethyl)-2,3-dimethoxy-phenyl]-1-[1-(6-methyl-pyridin-3-yl)-3,4-dihydro-1H-1isoquinolin-2-yl]-propenone.

11. The compound of claim 1 which is (E)-(RS)-3-[5-(2,4-diamino-pyrimidin-5-ylmethyl)-2,3-dimethoxy-phenyl]-1-[1-(4-dimethylamino-pyridin-2-yl)-3,4-dihydro-1H-1isoquinolin-2-yl]-propenone.

12. The compound of claim 1 which is (E)-(RS)-4-(2-{3-[5-(2,4-diamino-pyrimidin-5-ylmethyl)-2,3-dimethoxy-phenyl]-acryloyl}-1,2,3,4-tetrahydro-isoquinolin-1-yl)-benzamide.

13. The compound of claim 1 which is (E)-(RS)-3-[5-(2,4-diamino-pyrimidin-5-ylmethyl)-2,3-dimethoxy-phenyl]-1-[1-(4-methylsulphanyl-phenyl)-3,4-dihydro-1H-1isoquinolin-2-yl]-propenone.

14. The compound according to claim 1 which is (E)-(R)-3-[5-(2,4-diamino-pyrimidin-5-ylmethyl)-2,3-dimethoxy-phenyl]-1-(1-pyridin-2-yl-3,4-dihydro-1H-isoquinolin-2-yl)-propenone.

15. The compound according to claim 1 which is (E)-(RS)-3-[5-(2,4-diamino-pyrimidin-5-ylmethyl)-2,3-dimethoxy-phenyl]-1-(1-pyridin-2-yl-3,4-dihydro-1H-isoquinolin-2-yl)-propenone.

16. The compound according to claim 1 which is (E)-(RS)-3-[5-(2,4-diamino-pyrimidin-5-ylmethyl)-2,3-dimethoxy-phenyl]-1-(7-methoxy-1-pyridin-2-yl-3,4-dihydro-1H-1isoquinolin-2-yl)-propenone.

17. The compound according to claim 1 which is (E)-(RS)-3-[5-(2,4-diamino-pyrimidin-5-ylmethyl)-2,3-dimethoxy-phenyl]-1-[1-(4-methyl-phenyl)-3,4-dihydro-1H-isoquinolin-2-yl]-propenone.

18. The compound according to claim 1 which is (E)-(RS)-3-[5-(2,4-diamino-pyrimidin-5-ylmethyl)-2,3-dimethoxy-phenyl]-1-[1-(4-hydroxy-phenyl)-3,4-dihydro-1H-isoquinolin-2-yl]-propenone.

19. The compound according to claim 1 which is (E)-(RS)-4-[2-[3-[5-(2,4-diamino-pyrimidin-5-yl)-2,3-dimethoxy-phenyl]-acryloyl]-1,2,3,4-tetrahydro-isoquinolin-1-yl]-benzonitrile.

20. The compound according to claim 1 which is (E)-(RS)-3-[5-(2,4-diamino-pyrimidin-5-ylmethyl)-2,3-dimethoxy-phenyl]-1-(1-thiophen-2-yl-3,4-dihydro-1H-isoquinolin-2-yl)-propenone.

21. The compound according to claim 1 which is (E)-(RS)-1-[1-(5-chloro-pyridin-2-yl)-3,4-dihydro-1H-1isoquinolin-2-yl]-3-[5-(2,4-diamino-pyrimidin-5-ylmethyl)-2,3-dimethoxy-phenyl]-propenone.

22. The compound according to claim 1 which is (E)-(RS)-1-[1-(6-chloro-pyridin-3-yl)-3,4-dihydro-1H-1isoquinolin-2-yl]-3-[5-(2,4-diamino-pyrimidin-5-ylmethyl)-2,3-dimethoxy-phenyl]-propenone.

23. The compound according to claim 1 which is (E)-(RS)-5-[2-[3-[5-(2,4-diamino-pyrimidin-5-ylmethyl)-2,3-dimethoxy-phenyl]-acryloyl]-1,2,3,4-tetrahydro-isoquinolin-1-yl]-pyridin-2-carboxamide.

24. The compound according to claim 1 which is E)-(RS)-3-[5-(2,4-diamino-pyrimidin-5-ylmethyl)-2,3-dimethoxy-phenyl]-1-[1-(4-methanesulphonyl-phenyl)-3,4-dihydro-1H-1isoquinolin-2-yl]-propenone.

25. The compound according to claim 1 which is (E)-3-[5-(2,4-diamino- pyrimidin-5-ylmethyl)-2,3-dimethoxy-phenyl]-1-(3,4-dihydro-1H-1isoquinolin-2-yl)-propenone.

26. The compound according to claim 1 which is (E)-1-(7-chloro-3,4-dihydro-1H-1isoquinolin-2-yl)-3-[5-(2,4-diamino-pyrimidin-5-ylmethyl)-2,3-dimethoxy-phenyl]-propenone.

27. The compound according to claim 1 which is (E)-(RS)-3-[5-(2,4-diamino-pyrimidin-5-ylmethyl)-2,3-dimethoxy-phenyl]-1-(1-phenyl-3,4-dihydro-1H-1isoquinolin-2-yl)-propenone.

28. The compound according to claim 1 which is (E)-(RS)-3-[5-(2,4-diamino-pyrimidin-5-ylmethyl)-2,3-dimethoxy-phenyl]-1-(1-pyridin-4-yl-3,4-dihydro-1H-isoquinolin-2-yl)-propenone.

29. The compound according to claim 1 which is (E)-(RS)-3-[5-(2,4-diamino-pyrimidin-5-ylmethyl)-2,3-dimethoxy-phenyl]-1-(1-pyridin-3-yl-3,4-dihydro-1H-isoquinolin-2-yl)-propenone.

30. The compound according to claim 1 which is 3-[5-(2,4-diamino-pyrimidin-5-ylmethyl)-2,3-dimethoxy-phenyl]-1-(3,4-dihydro-1H-1isoquinolin-2-yl)-propynone.

31. The compound according to claim 1 which is (E)-(RS)-3-[5-(2,4-diamino-pyrimidin-5-ylmethyl)-2,3-dimethoxy-phenyl]-1-(1-pyrazin-2-yl-3,4-dihydro-1H-isoquinolin-2-yl)-propenone.

32. The compound according to claim 1 which is (E)-(RS)-1-(7-chloro-1-pyridin-2-yl-3,4-dihydro-1H-1isoquinolin-2-yl)-3-[5-(2,4-diamino-pyrimidin-5-ylmethyl)-2,3-dimethoxy-phenyl]-propenone.

33. The compound according to claim 1 which is(E)-(RS)-3-[5-(2,4-diamino-pyrimidin-5-ylmethyl)-2,3-dimethoxy-phenyl]-1-(7-methyl-1-pyridin-2-yl-3,4-dihydro-1H-isoquinolin-2-yl)-propenone.

34. The compound according to claim 1 which is (E)-(RS)-1-[1-(4-chloro-phenyl)-3,4-dihydro-1H-1isoquinolin-2-yl]-3-[5-(2,4-diamino-pyrimidin-5-ylmethyl)-2,3-dimethoxy-phenyl]-propenone.

35. The compound according to claim 1 which is (E)-(RS)-1-(1-cyclohexyl-3,4-dihydro-1H-1isoquinolin-2-yl)-3-[5-(2,4-diamino-pyrimidin-5-ylmethyl)-2,3-dimethoxy-phenyl]-propenone.

36. The compound according to claim 1 which is (E)-(RS)-3-[5-(2,4-diamino-pyrimidin-5-ylmethyl)-2,3-dimethoxy-phenyl]-1-(1-pyrimidin-5-yl-3,4-dihydro-1H-isoquinolin-2-yl)-propenone hydrochloride.

37. The compound according to claim 1 which is (E)-(RS)-3-[5-(2,4-diamino-pyrimidin-5-ylmethyl)-2,3-dimethoxy-phenyl]-1-(1-pyrimidin-4-yl-3,4-dihydro-1H-isoquinolin-2-yl)-propenone.

38. The compound according to claim 1 which is (E)-(RS)-1-(1-benzyl-3,4-dihydro-1H-1isoquinolin-2-yl)-3-[5-(2,4-diamino-pyrimidin-5-ylmethyl)-2,3-dimethoxy-phenyl]-propenone.

39. The compound according to claim 1 which is (E)-(RS)-3-[5-(2,4-diamino-pyrimidin-5-ylmethyl)-2,3-dimethoxy-phenyl]-1-(1-isobutyl-3,4-dihydro-1H-isoquinolin-2-yl)-propenone.

40. The compound according to claim 1 which is (E)-(RS)-3-[5-(2,4-diamino-pyrimidin-5-ylmethyl)-2,3-dimethoxy-phenyl]-1-[1-(4-methoxy-phenyl)-3,4-dihydro-1H-isoquinolin-2-yl]-propenone.

41. The compound according to claim 1 which is (E)-(RS)-3-[5-(2,4-diamino-pyrimidin-5-ylmethyl)-2,3-dimethoxy-phenyl]-1-[1-(4-dimethylamino-phenyl)-3,4-dihydro-1H-1isoquinolin-2-yl]-propenone.

42. The compound according to claim 1 which is (E)-(RS)-3-[5-(2,4-diamino-pyrimidin-5-ylmethyl)-2,3-dimethoxy-phenyl]-1-(1-pyridazin-3-yl-3,4-dihydro-1H-isoquinolin-2-yl)-propenone.

43. The compound according to claim 1 which is (E)-(RS)-3-[5-(2,4-diamino-pyrimidin-5-ylmethyl)-2,3-dimethoxy-phenyl]-1-(1-pyridazin-4-yl-3,4-dihydro-1H-isoquinolin-2-yl)-propenone.

44. The compound according to claim 1 which is (E)-(RS)-2-[3-[5-(2,4-diamino-pyrimidin-5-ylmethyl)-2,3-dimethoxy-phenyl]-acryloyl]-1,2,3,4-tetrahydro-isoquinoline-1-carbonitrile.

45. The compound according to claim 1 which is (E)-(RS)-3-[5-(2,4-diamino-pyrimidin-5-ylmethyl)-2,3-dimethoxy-phenyl]-1-[1-(4-trifluoromethyl-phenyl)-3,4-dihydro-1H-1isoquinolin-2-yl]-propenone.

46. The compound according to claim 1 which is (E)-(RS)-3-[5-(2,4-diamino-pyrimidin-5-ylmethyl)-2,3-dimethoxy-phenyl]-1-[1-(6-hydroxy-pyridin-3-yl)-3,4-dihydro-1H-isoquinolin-2-yl]-propenone trifluoroacetate.

47. The compound according to claim 1 which is ethyl (E)-(RS)-4-[2-[3-[5-(2,4-diamino-pyrimidin-5-ylmethyl)-2,3-dimethoxy-phenyl]-acryloyl]-1,2,3,4-tetrahydro-isoquinolin-1-yl]-benzoate.

48. The compound according to claim 1 which is (E)-(RS)-1-[1-(4-chloro-pyridin-2-yl)-3,4-dihydro-1H- isoquinolin-2-yl]-3-[5-(2,4-diamino-pyrimidin-5-ylmethyl)-2,3-dimethoxy-phenyl]-propenone.

49. The compound according to claim 1 which is (E)-(RS)-3-[5-(2,4-diamino-pyrimidin-5-ylmethyl)-2,3-dimethoxy-phenyl]-1-[1-(6-dimethylamino-pyridin-3-yl)-3,4-dihydro-1H-1isoquinolin-2-yl]-propenone.

50. The compound according to claim 1 which is (E)-(RS)-3-[5-(2,4-diamino- pyrimidin-5-ylmethyl)-2-hydroxy-3-methoxy-phenyl]-1-(1-pyridin-2-yl-3,4-dihydro-1H-isoquinolin-2-yl)-propenone.

51. The compound according to claim 1 which is (E)-(RS)-3-[5-(2,4-diamino-pyrimidin-5-ylmethyl)-2,3-dimethoxy-phenyl]-1-[1-(4-diethylaminomethyl-phenyl)-3,4-dihydro-1H-1isoquinolin-2-yl]-propenone.

52. The compound according to claim 1 which is (E)-(RS)-3-[5-(2,4-diamino-pyrimidin-5-ylmethyl)-2,3-dimethoxy-phenyl]-1-[1-(4-methoxy-pyridin-2-yl)-3,4-dihydro-1H-1isoquinolin-2-yl]-propenone.

53. The compound according to claim 1 which is (E)-(RS)-5-(2-{3-[5-(2,4-diamino-pyrimidin-5-ylmethyl)-2,3-dimethoxy-phenyl]-acryloyl}-1,2,3,4-tetrahydro-isoquinolin-1-yl)-pyridine-2-carboxamide.

54. The compound according to claim 1 which is (E)-(RS)-3-[5-(2,4-diamino-pyrimidin-5-ylmethyl)-2,3-dimethoxy-phenyl]-1-[1-(4-methanesulphonyl-phenyl)-3,4-dihydro-1H-1isoquinolin-2-yl]-propenone.

55. The compound according to claim 1 which is (E)-(RS)-3-[5-(2,4-diamino-pyrimidin-5-ylmethyl)-2,3-dimethoxy-phenyl]-1-[1-(6-morpholin-4-yl-pyridin-3-yl)-3,4-dihydro-1H-1isoquinolin-2-yl]-propenone.

56. The compound according to claim 1 which is (E)-(RS)-3-[5-(2,4-diamino-pyrimidin-5-ylmethyl)-2,3-dimethoxy-phenyl]-1-[1-(4-fluoro-phenyl)-3,4-dihydro-1H-isoquinolin-2-yl]-propenone.

57. The compound according to claim 1 which is (E)-(RS)-3-[5-(2,4-diamino-pyrimidin-5-ylmethyl)-2,3-dimethoxy-phenyl]-1-{1-[6-(4-methyl-piperazin-1-yl)-pyridin-yl]-3,4-dihydro-1H-1isoquinolin-2-yl}-propenone.

58. The compound according to claim 1 which is (E)-(RS)-3-[5-(2,4-diamino-pyrimidin-5-ylmethyl)-2,3-dimethoxy-phenyl]-1-[1-(4-morpholin-4-ylmethyl-phenyl)-3,4-dihydro-1H-1isoquinolin-2-yl)]-propenone.

59. The compound according to claim 1 which is (E)-(RS)-3-[5-(2,4-diamino-pyrimidin-5-ylmethyl)-2,3-dimethoxy-phenyl]-1-{1-[4-(4-methyl-piperazin-1-ylmethyl)-phenyl]-3,4-dihydro-1H-1isoquinolin-2-yl}-propenone.

60. The compound according to claim 1 which is (E)-(RS)-3-[5-(2,4-diamino-pyrimidin-5-ylmethyl)-2,3-dimethoxy-phenyl]-1-[1-(4-imidazol-1-yl-phenyl)-3,4-dihydro-1H-1isoquinolin-2-yl]-propenone.

61. The compound according to claim 1 which is (E)-(RS)-3-[5-(2,4-diamino-pyrimidin-5-ylmethyl)-2,3-dimethoxy-phenyl]-1-[1-(4-imidazol-1-ylmethyl-phenyl)-3,4-dihydro-1H-1isoquinolin-2-yl]-propenone.

62. The compound according to claim 1 which is (E)-(RS)-3-[5-(2,4-diamino-pyrimidin-5-ylmethyl)-2,3-dimethoxy-phenyl]-1-[1-(4-[1,2,4]triazol-1-yl-phenyl)-3,4-dihydro-1H-isoquinolin-2-yl]-propenone.

63. The compound according to claim 1 which is (E)-(RS)-3-[5-(2,4-diamino-pyrimidin-5-ylmethyl)-2,3-dimethoxy-phenyl]-1-[1-(4-[1,2,4]triazol-1-ylmethyl-phenyl)-3,4-dihydro-1H-isoquinolin-2-yl]-propenone.

64. The compound according to claim 1 which is (E)-(RS)-3-[5-(2,4-diamino-pyrimidin-5-ylmethyl)-2,3-dimethoxy-phenyl]-1-[1-(3-methanesulfonyl-phenyl)-3,4-dihydro-1H-isoquinolin-2-yl]-propenone.

65. The compound according to claim 1 which is (E)-(RS)-3-[5-(2,4-diamino-pyrimidin-5-ylmethyl)-2,3-dimethoxy-phenyl]-1-[1-(6-methylsulphanyl-pyridin-3-yl)-3,4-dihydro-1H-isoquinolin-2-yl]-propenone.

66. The compound according to claim 1 which is (E)-(RS)-3-[5-(2,4-diamino-pyrimidin-5-ylmethyl)-2,3-dimethoxy-phenyl]-1-1-{6[(2-hydroxy-ethyl)-methyl-amino]-pyridin-3-yl}-3,4-dihydro-1H-isoquinolin-2-yl)]-propenone.

67. The compound according to claim 1 which is (E)-(RS)-3-[5-(2,4-diamino-pyrimidin-5-ylmethyl)-2,3-dimethoxy-phenyl]-1-(1-methyl-3,4-dihydro-1H-isoquinolin-2-yl)-propenone.

68. The compound according to claim 1 which is (E)-(RS)-3-[5-(2,4-diamino-pyrimidin-5-ylmethyl)-2,3-dimethoxy-phenyl]-1-[1-(4-hydroxymethyl-phenyl)-3,4-dihydro-1H-isoquinolin-2-yl]-propenone.

69. The compound according to claim 1 which is (E)-(RS)-3-[5-(2,4-diamino-pyrimidin-5-ylmethyl)-2,3-dimethoxy-phenyl]-1-(1-ethyl-3,4-dihydro-1H-isoquinolin-2-yl)-propenone.

70. The compound according to claim 1 which is (E)-(RS)-3-[5-(2,4-diamino-pyrimidin-5-ylmethyl)-2,3-dimethoxy-phenyl]-1-[1-(2-methyl-4-morpholin-4-ylmethyl-2H-pyrazol-3-yl)-3,4-dihydro-1H-isoquinolin-2-yl]-propenone.

71. The compound according to claim 1 which is (E)-(RS)-3-[5-(2,4-diamino-pyrimidin-5-ylmethyl)-2,3-dimethoxy-phenyl]-1-[1-[1-methyl-5-(4-methyl-piperazin-1-ylmethyl)-1H-pyrazol-3-yl]-3,4-dihydro-1H-isoquinolin-2-yl]-propenone.

72. The compound according to claim 1 which is (E)-(RS)-3-[5-(2,4-diamino-pyrimidin-5-ylmethyl)-2,3-dimethoxy-phenyl]-1-[1-(1-methyl-4-morpholin-4-ylmethyl-1-H-pyrazol-3-yl)-3,4-dihydro-1H-isoquinolin-2-yl]-propenone.

73. The compound according to claim 1 which is (E)-(RS)-3-[5-(2,4-diamino-pyrimidin-5-ylmethyl)-2,3-dimethoxy-phenyl]-1-[1-(2-methyl-5-morpholin-4-ylmethyl-2H-pyrazol-3-yl)-3,4-dihydro-1H-isoquinolin-2-yl]-propenone.

74. The compound according to claim 1 which is (E)-(RS)-2-[5-[2-[3-[5-(2,4-diamino-pyrimidin-5-ylmethyl)-2,3-dimethoxyphenyl]-acryloyl]-1,2,3,4-tetrahydro-isoquinolin-1-yl]-1-methyl-1H-pyrazol-3-yl]-acetamide.

75. The compound according to claim 1 which is (E)-(RS)-3-[5-(2,4-diamino-pyrimidin-5-ylmethyl)-2,3-dimethoxy-phenyl]-1-[1-(1-methyl-5-morpholin-4-ylmethyl-1H-pyrazol-3-yl)-3,4-dihydro-1H-isoquinolin-2-yl]-propenone.

76. The compound according to claim 1 which is (E)-(RS)-3-[5-(2,4-diamino-pyrimidin-5-ylmethyl)-2,3-dimethoxy-phenyl]-1-[1-[5-(2-hydroxy-ethyl)-2-methyl-2H-pyrazol-3-yl]-3,4-dihydro-1H-isoquinolin-2-yl]-propenone.

77. The compound according to claim 1 which is methyl (E)-(RS)-[5-[2-[3-[5-(2,4-diamino-pyrimidin-5-ylmethyl)-2,3-dimethoxy-phenyl]-acryloyl]-1,2,3,4-tetrahydro-isoquinolin-1-yl]-1-methyl-1H-pyrazol-3-yl]-acetate.

78. The compound according to claim 1 which is (E)-(RS)-3-[5-(2,4-diamino-pyrimidin-5-ylmethyl)-2,3-dimethoxy-phenyl]-1-[1-(5-hydroxymethyl-2-methyl-2H-pyrazol-3-yl)-3,4-dihydro-1H-isoquinolin-2-yl]-propenone.

79. A process for manufacturing a compound of the formula:

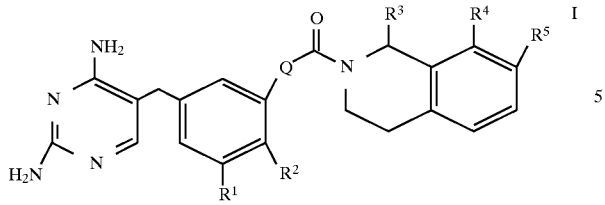

wherein $R^1$ is $C_1$–$C_6$ alkoxy;

$R^2$ is bromine, $C_1$–$C_6$ alkoxy, or hydroxy;

$R^3$ is hydrogen, $C_1$–$C_6$ alkyl, cycloalkyl, aryl, heterocyclyl, aralkyl, heterocyclyl $C_1$–$C_6$ alkyl, or cyano, wherein aryl is selected from the group consisting of phenyl; phenyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; naphthyl; naphthyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; anthryl; anthryl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; phenanthryl; phenanthryl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; 2H-tetrazol-5-yl-phenyl; 4-morpholin-4-yl-methyl-phenyl; 4-methyl-piperazin-1-yl-methyl-phenyl; 4-imidazo-1-yl-phenyl; 4-imidazo-1-yl-methyl-phenyl; triazol-1-yl-phenyl; and 1,2,4-triazol-1-yl-methyl-phenyl; and heterocyclyl is selected from the group consisting of furyl; furyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$-$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyranyl; pyranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; thienyl; thienyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyrrolyl; pyrrolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyrazolyl; pyrazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; imidazolyl; imidazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; thiazolyl; thiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; tetrazolyl; tetrazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; oxazolyl; oxazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; oxadiazolyl; oxadiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; isoxazolyl; isoxazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; thiazolyl; thiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; isothiazolyl; isothiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyridyl; pyridyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyridazinyl; pyridazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyrimidinyl; pyrimidinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyrazinyl; pyrazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; triazinyl; triazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; benzopyranyl; benzopyranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; benzofuranyl; benzofuranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; indolyl; indolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; quinolinyl; quinolinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; 2-pyridin-3-yl-thiazol; 1-benzyl-5-methyl-1H-pyrazol-3-yl; 5-furan-2-yl-thiazol-4-yl; 5-pyridin-2-yl-thiophen- 2-yl; 6-morpholin-4-yl-pyridin-3-yl; 4-methyl-piperazin-1-yl-pyridin-3-yl; 4-methyl-piperazin-1-yl-methyl-1H-pyrazol-3-yl; 2-methyl-4-morpholin-4-yl-methyl-2H-pyrazol-3-yl; morpholin-4-yl; 4-methyl-piperazin-1-yl; imidazol-1-yl; [1,2,4]triazol-1-yl; tetrazol; morpholin-4-yl-methyl; 4-methyl-piperazin-1-yl-methyl; imidazol-1-yl-methyl; [1,2,4]triazol-1-yl-methyl; and cyclo($C_3$–$C_6$ alkyl)amino;

$R^4$ is hydrogen, $C_1$–$C_6$ alkyl, $C_1$–$C_6$ alkoxy, halogen, hydroxy, amino, di($C_1$–$C_6$ alkyl)amino, cyano, or nitro;

$R^5$ is hydrogen, $C_1$–$C_6$ alkyl, $C_1$–$C_6$ alkoxy, halogen, hydroxy, amino, di($C_1$–$C_6$ alkyl)amino, cyano, or nitro; and Q is ethynyene or vinylene;

which process comprises:

reacting a compound of the formula

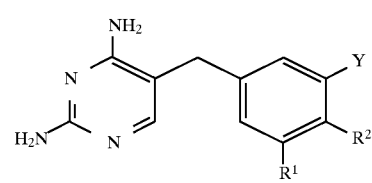

II with a compound of the formula

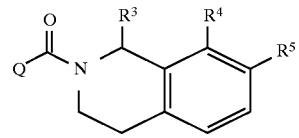

III in which $R^1$–$R^5$ and Q are as set forth above and Y represents a leaving group.

80. The method of claim 79, wherein the leaving group Y is selected from the group consisting of bromine, iodine, methanesulphonyloxy, trifluoromethanesulphonyloxy, benzenesulphonyloxy, and p-toluenesulphonyloxy.

81. The method of claim 79, wherein the reacting is performed in the presence of a base.

82. The method of claim 81, wherein the base is an alkali metal carbonate or a tertiary amine.

83. The method of claim 82, wherein the base is selected from the group consisting of potassium carbonate, triethylamine, or tri-n-butylamine.

84. The method of claim 82, wherein the reaction is performed in the presence of a catalyst.

85. The method of claim 85, wherein the catalyst is a palladium catalyst.

86. The method of claim 85, wherein the palladium catalyst is selected from the group consisting of palladium (II) acetate; bis(triphenylphosphine)palladium (II) dichloride; bis(triphenylphosphine)palladium (II) diacetate; tetrakistriphenylphosphinepalladium; copper (I) iodine and triphenylphosphine; and copper (I) iodine and tri-o-tolylphosphine.

87. The method of claim 84 further comprising reacting in the presence of a phase transfer catalyst.

88. The method of claim 87, wherein the phase transfer catalyst is a tetraalkylammonium salt.

89. The method of claim 79, wherein the reacting is performed in an inert organic solvent.

90. The method of claim 89, wherein the inert organic solvent is selected from the group consisting of dioxan, tetrahydrofuran, N,N-dimethylacetamide, and N,N-dimethylformamide.

91. The method of claim 79, wherein the reacting is at a temperature between about 40° C. and the boiling point of the reaction mixture.

92. A method of treating or preventing infectious diseases associated with infection by *S. aureus* or *P. carinii*, which comprises administering to a subject an effective amount of a compound of the formula.

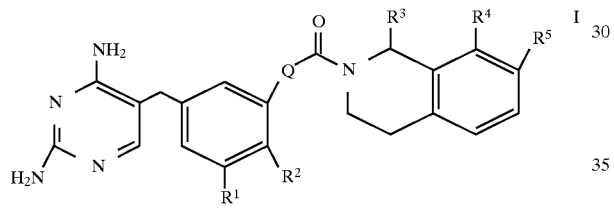

wherein $R^1$ is $C_1-C_6$ alkoxy;

$R^2$ is bromine, $C_1-C_6$ alkoxy, or hydroxy;

$R^3$ is hydrogen, $C_1-C_6$ alkyl, cycloalkyl, aryl, heterocyclyl, aralkyl, heterocyclyl $C_1-C_6$ alkyl, or cyano, wherein aryl is selected from the group consisting of phenyl; phenyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; naphthyl; naphthyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; anthryl; anthryl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl) carbamoyl, $C_1-C_6$ alkylsulfanyl, $C_1-C_6$ alkylsulfonyl, sulfamoyl, N-mono-($C_1-C_6$ alkyl) sulfamoyl, or di-($C_1-C_6$ alkyl)sulfamoyl; phenanthryl; phenanthryl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl) carbamoyl, $C_1-C_6$ alkylsulfanyl, $C_1-C_6$ alkylsulfonyl, sulfamoyl, N-mono-($C_1-C_6$ alkyl) sulfamoyl, or di-($C_1-C_6$ alkyl)sulfamoyl; 2H-tetrazol-5-yl-phenyl; 4-morpholin-4-yl-methyl-phenyl; 4-methyl-piperazin-1-yl-methyl-phenyl; 4-imidazo-1-yl-phenyl; 4-imidazo-1-yl-methyl-phenyl; triazol-1- yl-phenyl; and 1,2,4-triazol-1-yl-methyl-phenyl; and heterocyclyl is selected from the group consisting of furyl; furyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; pyranyl; pyranyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; thienyl; thienyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; pyrrolyl; pyrrolyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; pyrazolyl; pyrazolyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; imidazolyl; imidazolyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl) carbamoyl, $C_1-C_6$ alkylsulfanyl, $C_1-C_6$ alkylsulfonyl, sulfamoyl, N-mono-($C_1-C_6$ alkyl) sulfamoyl, or di-($C_1-C_6$ alkyl)sulfamoyl; thiazolyl; thiazolyl substituted with phenyl, $C_1-C_6$ alkyl, $C_3-C_6$ cycloalkyl, halogen, trifluoromethyl, $C_1-C_6$ alkoxy, $C_1-C_6$ alkoxy-carbonyl, hydroxy, di($C_1-C_6$ alkyl) amino, cyano, carbamoyl, mono-($C_1-C_6$ alkyl)carbamoyl, di-($C_1-C_6$ alkyl)carbamoyl, $C_1-C_6$ alkylsulfanyl, $C_1-C_6$ alkylsulfonyl, sulfamoyl, N-mono-($C_1-C_6$ alkyl)sulfamoyl, or di-($C_1-C_6$ alkyl)sulfamoyl; tetrazolyl; tetrazolyl substituted with phenyl, $C_1-C_6$ alkyl, $C_3-C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; oxazolyl; oxazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; oxadiazolyl; oxadiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; isoxazolyl; isoxazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; thiazolyl; thiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; isothiazolyl; isothiazolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; pyridyl; pyridyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyridazinyl; pyridazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyrimidinyl; pyrimidinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; pyrazinyl; pyrazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; triazinyl; triazinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; benzopyranyl; benzopyranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; benzofuranyl; benzofuranyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; indolyl; indolyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl) carbamoyl, $C_1$–$C_6$ alkylsulfanyl, $C_1$–$C_6$ alkylsulfonyl, sulfamoyl, N-mono-($C_1$–$C_6$ alkyl) sulfamoyl, or di-($C_1$–$C_6$ alkyl)sulfamoyl; quinolinyl; quinolinyl substituted with phenyl, $C_1$–$C_6$ alkyl, $C_3$–$C_6$ cycloalkyl, halogen, trifluoromethyl, $C_1$–$C_6$ alkoxy, $C_1$–$C_6$ alkoxy-carbonyl, hydroxy, di($C_1$–$C_6$ alkyl) amino, cyano, carbamoyl, mono-($C_1$–$C_6$ alkyl)carbamoyl, di-($C_1$–$C_6$ alkyl)carbamoyl, $C_1$–$C_6$ alkylsulfanyl, $C_1$–$C_6$ alkylsulfonyl, sulfamoyl, N-mono-($C_1$–$C_6$ alkyl)sulfamoyl, or di-($C_1$–$C_6$ alkyl)sulfamoyl; 2-pyridin-3-yl-thiazol; 1-benzyl-5-methyl-1H-pyrazol-3-yl; 5-furan-2-yl-thiazol-4-yl; 5-pyridin-2-yl-thiophen-2-yl; 6-morpholin-4-yl-pyridin-3-yl; 4-methyl-piperazin-1-yl-pyridin-3-yl; 4-methyl-piperazin-1-yl-methyl-1H-pyrazol-3-yl; 2-methyl-4-morpholin-4-yl-methyl-2H-pyrazol-3-yl; morpholin-4-yl; 4-methyl-piperazin-1-yl; imidazol-1-yl; [1,2,4]triazol-1-yl; tetrazol; morpholin-4-yl-methyl; 4-methyl-piperazin-1-yl-methyl; imidazol-1-yl-methyl; [1,2,4]triazol-1-yl-methyl; and cyclo($C_3$–$C_6$ alkyl)amino;

$R^4$ is hydrogen, $C_1$–$C_6$ alkyl, $C_1$–$C_6$ alkoxy, halogen, hydroxy, amino, di($C_1$–$C_6$ alkyl)amino, cyano, or nitro;

$R^5$ is hydrogen, $C_1$–$C_6$ alkyl, $C_1$–$C_6$ alkoxy, halogen, hydroxy, amino, di($C_1$–$C_6$ alkyl)amino, cyano, or nitro; and Q is ethynyene or vinylene;

or a pharmaceutically usable salt thereof.

* * * * *

UNITED STATES PATENT AND TRADEMARK OFFICE
CERTIFICATE OF CORRECTION

PATENT NO. : 5,866,583
DATED : February 2, 1999
INVENTOR(S) : Guerry et al

It is certified that error appears in the above-identified patent and that said Letters Patent is hereby corrected as shown below:

Column 33, claim 21, line 30, "1isoquinolin-2-yl]" should be -- isoquinolin-2-yl]- --;

claim 22, line 24, "1isoquinolin-2-yl]" should be -- isoquinolin-2-yl]- -- claim 24, line 40, "E)-(RS)" should be -- (E)-(RS) --;

claim 24, line 43, "1H-1isoquinolin-2-yl]" should be -- 1H-isoquinolin-2-yl]- --;

claim 25, line 46, "1h-1isoquinolin-2-yl]-" should be -- 1H-isoquinolin-2-yl]- --;

claim 26, line 48, "1H-1isoquinolin-2-yl)-" should be -- 1H-isoquinolin-2-yl)- --;

claim 27, line 54, "1isoquinolin-2-yl)" should be -- isoquinolin-2-yl)- --;

claim 30, line 65, "1isoquinolin-2-yl)" should be -- isoquinolin-2-yl)- --;

UNITED STATES PATENT AND TRADEMARK OFFICE
CERTIFICATE OF CORRECTION

PATENT NO. : 5,866,583
DATED : February 2, 1999
INVENTOR(S) : Guerry et al

It is certified that error appears in the above-identified patent and that said Letters Patent is hereby corrected as shown below:

Column 34, claim 32, line 5, "1isoquinolin-2-yl)" should be -- isoquinolin-2-yl)- --;

claim 34, line 12, "1isoquinolin" should be -- isoquinolin --;

claim 35, line 16, "1isoquinolin-2-yl)" should be -- isoquinolin-2-yl)- --;

claim 38, line 27, "1isoquinolin-2-yl)" should be -- isoquinolin-2-yl)- --;

claim 41, line 41, "1isoquinolin-2-yl]" should be -- isoquinolin-2-yl]- --;

claim 45, line 57, "1isoquinolin-2-yl]" should be -- isoquinolin-2-yl]- --;

Column 35, claim 49, line 6, "1isoquinolin-2-yl]" should be -- isoquinolin-2-yl]- --;

claim 51, line 14, "1isoquinolin-2-yl]" should be -- isoquinolin-2-yl]- --;

claim 52, line 18, "1isoquinolin-2-yl]" should be -- isoquinolin-2-yl]- --;

claim 54, line 27, "1isoquinolin-2-yl]" should be -- isoquinolin-2-yl]- --;

claim 55, line 30, "1isoquinolin-2-yl]" should be -- isoquinolin-2-yl]- --;

claim 57, line 38, "-1H-1isoquinolin-2-yl}" should be -- -1H-isoquinolin-2-yl}- --;

UNITED STATES PATENT AND TRADEMARK OFFICE
CERTIFICATE OF CORRECTION

PATENT NO. : 5,866,583
DATED : February 2, 1999
INVENTOR(S) : Guerry, et al.

It is certified that error appears in the above-indentified patent and that said Letters Patent is hereby corrected as shown below:

claim 58, line 42, "-1H-1isoquinolin-2-yl]" should be -- -1H- isoquinolin-2-yl]- --;

claim 59, line 46, "-1H-1isoquinolin-2-" should be -- -1H-isoquinolin-2- --;
claim 60, line 51, "-1H-1isoquinolin-2-" should be -- -1H-isoquinolin-2- --;
claim 61, line 55, "-1H-1isoquinolin-2-" should be -- -1H-isoquinolin-2- --;

Signed and Sealed this

Thirtieth Day of November, 1999

Attest:

Attesting Officer

Q. TODD DICKINSON

Acting Commissioner of Patents and Trademarks